US005696250A

United States Patent [19]

Elliott

[11] Patent Number: 5,696,250

[45] Date of Patent: Dec. 9, 1997

[54] DNA ENCODING MEGAKARYOCYTE GROWTH AND DEVELOPMENT FACTOR ANALOGS

[75] Inventor: Steven G. Elliott, Newbury Park, Calif.

[73] Assignee: Amgen Inc., Thousand Oaks, Calif.

[21] Appl. No.: 388,779

[22] Filed: Feb. 15, 1995

[51] Int. Cl.[6] .......... C12N 15/19; C07K 14/52

[52] U.S. Cl. .......... 536/23.5; 435/69.5; 435/325; 435/252.3; 435/320.1; 935/11; 935/27; 935/66; 935/70

[58] Field of Search .......... 536/23.1, 23.5; 435/69.5, 172.3, 240.2, 252.3, 320.1; 935/11, 22, 27, 66, 70

[56] References Cited

U.S. PATENT DOCUMENTS

| | | | |
|---|---|---|---|
| 5,217,881 | 6/1993 | Park | 435/69.5 |
| 5,218,092 | 6/1993 | Sasaki et al. | 530/351 |

FOREIGN PATENT DOCUMENTS

| | | |
|---|---|---|
| 0 428 267 A2 | 10/1990 | European Pat. Off. . |
| WO 95/05465 | 2/1995 | WIPO . |
| WO 95/18858 | 7/1995 | WIPO . |
| WO 95/21919 | 8/1995 | WIPO . |
| WO 95/21920 | 8/1995 | WIPO . |
| WO 95/26746 | 10/1995 | WIPO . |

OTHER PUBLICATIONS

Lok et al. (1994) Nature vol. 369 pp. 565–568.

Bose et al. (1976) J. of Biol. Chem. vol. 251, No. 6, pp. 1659–1662.

Chang et al. (1995). J. of Biol. Chem. vol. 270, No. 2, pp. 511–514.

Delorme et al. (1992) *Biochemistry* 31/41:9871–9876.

*Primary Examiner*—John Ulm
*Assistant Examiner*—Prema Mertz
*Attorney, Agent, or Firm*—Robert R. Cook; Ron K. Levy; Steven Odre

[57] ABSTRACT

MGDF analogs having one or more changed glycosylation sites as compared to a naturally occuring MGDF sequence of a corresponding number of amino acids are disclosed. The invention also relates to DNA sequences encoding said MGDF analogs, recombinant plasmids and host cells for analog expression, and therapeutic compositions including such analogs.

7 Claims, 9 Drawing Sheets

```
  1   CAGGGAGCCACGCCAGCCAAGACACCCCGGCCAGAATGGAGCTGACTGAATTGCTCCTC  53
-21                                  MetGluLeuThrGluLeuLeuLeu  -14

 70   GTGGTCATGCTTCTCCTAACTGCAAGGCTAACGCTGTCCAGCCCGGCTCCTCCTGCTTGT  119
-13   ValValMetLeuLeuLeuThrAlaArgLeuThrLeuSerSerProAlaProProAlaCys  7

120   GACCTCCGAGTCCTCAGTAAACTGCTTCGTGACTCCCATGTCCTTCACAGCAGACTGAGC  179
  8   AspLeuArgValLeuSerLysLeuLeuArgAspSerHisValLeuHisSerArgLeuSer  27

180   CAGTGCCCAGAGGTTCACCCTTTGCCTACACCTGTCCTGCTGCCTGCTGTGGACTTTAGC  239
 28   GlnCysProGluValHisProLeuProThrProValLeuLeuProAlaValAspPheSer  47

240   TTGGGAGAATGGAAAACCCAGATGGAGGAGACCAAGGCACAGGACATTCTGGGAGCAGTG  299
 48   LeuGlyGluTrpLysThrGlnMetGluGluThrLysAlaGlnAspIleLeuGlyAlaVal  67

300   ACCCTTCTGCTGGAGGGAGTGATGGCAGCACGGGGACAACTGGGACCCACTTGCCTCTCA  359
 68   ThrLeuLeuLeuGluGlyValMetAlaAlaArgGlyGlnLeuGlyProThrCysLeuSer  87

360   TCCCTCCTGGGGCAGCTTTCTGGACAGGTCCGTCTCCTCCTTGGGGCCCTGCAGAGCCTC  419
 88   SerLeuLeuGlyGlnLeuSerGlyGlnValArgLeuLeuLeuGlyAlaLeuGlnSerLeu  107
```

FIG. 1A

```
420  CTTGGAACCCAGCTTCCTCACAGGGCAGGACCACAGCTCACAAGGATCCCAATGCCATCC  479
108  LeuGlyThrGlnLeuProProGlnGlyArgThrThrAlaHisLysAspProAsnAlaIle  127

480  TTCCTGAGCTTCCAACACCTGCTCCGAGGAAAGGTGCGTTTCCTGATGCTTGTAGGAGGG  539
128  PheLeuSerPheGlnHisLeuLeuArgGlyLysValArgPheLeuMetLeuValGlyGly  147

540  TCCACCCTCTGCGTCAGGCGGGCCCCACCCACCACAGCTGTCCCCAGCAGAACCTCTCTA  599
148  SerThrLeuCysValArgArgAlaProProThrThrAlaValProSerArgThrSerLeu  167

600  GTCCTCACACTGAACGAGCTCCCAAACAGGACTTCTGGATTGTTGGAGACAAACTTCACT  659
168  ValLeuThrLeuAsnGluLeuProAsnArgThrSerGlyLeuLeuGluThrAsnPheThr  187

660  GCCTCAGCCAGAACTACTGGCTCTGGGCTTCTGAAGTGGCAGCAGGGATTCAGAGCCAAG  719
188  AlaSerAlaArgThrThrGlySerGlyLeuLeuLysTrpGlnGlnGlyPheArgAlaLys  207

720  ATTCCTGGTCTGCTGAACCAAACCTCCAGGTCCCTGGACCAAATCCCCGGATACCTGAAC  779
208  IleProGlyLeuLeuAsnGlnThrSerArgSerLeuAspGlnIleProGlyTyrLeuAsn  227

780  AGGATACACGAACTCTTGAATGGAACTCGTGGACTCTTTCCTGGACCCTCACGCAGGACC  839
228  ArgIleHisGluLeuLeuAsnGlyThrArgGlyLeuPheProGlyProSerArgArgThr  247
```

FIG. 1B

```
840   CTAGGAGCCCCGGACATTTCCTCAGGAACATCAGACACAGGCTCCCTGCCACCCAACCTC   899
248   LeuGlyAlaProAspIleSerSerGlyThrSerAspThrGlySerLeuProProAsnLeu   267

900   CAGCCTGGATATTCTCCTTCCCCAACCCATCCTCCTACTGGACAGTATACGCTCTTCCCT   959
268   GlnProGlyTyrSerProSerProThrHisProProThrGlyGlnTyrThrLeuPhePro   287

960   CTTCCACCCACCTTGCCCACCCCTGTGGTCCAGCTCCACCCCCTGCTTCCTGACCCTTCT   1019
288   LeuProProThrLeuProThrProValValGlnLeuHisProLeuLeuProAspProSer   307

1020  GCTCCAACGCCCACCCCTACCAGCCCTCTTCTAAACACATCCTACACCCACTCCCAGAAT   1079
308   AlaProThrProThrProThrSerProLeuLeuAsnThrSerTyrThrHisSerGlnAsn   327

1080  CTGTCTCAGGAAGGGTAAGGTTCTCAGACACTGCCGACATCAGCATTGTCTCGTGTACAG   1139
329   LeuSerGlnGluGlyEnd
1140  CTCCCTTCCCTGCAGGGCGCCCCTGGGAGACAACTGGACAAGATTTCCTACTTTCTCCTG   1199
1200  AAACCCAAAGCCCTGGTAAAAGGGATACACAGGACTGAAAAGGGAATCATTTTTCACTGT   1259
1260  ACATTATAAACCTTCAGAAGCTATTTTTTTAAGCTATCAGCAATACTCATCAGAGCAGCT   1319
1320  AGCTCTTTGGTCTATTTTCTGCA     1342
```

FIG.1C

```
        10                  30                  50
         .         .         .         .         .         .
TCTAGACCACCATGGAGCTGACTGAATTGCTCCTCGTGGTCATGCTTCTCCTAACTGCAA
          M  E  L  T  E  L  L  L  V  V  M  L  L  L  T  A  R

        70                  90                 110
         .         .         .         .         .         .
GGCTAACGCTGTCCAGCCCGGCTCCTCCTGCTTGTGACCTCCGAGTCCTCAGTAAACTGC
 L  T  L  S  S  P  A  P  P  A  C  D  L  R  V  L  S  K  L  L

       130                 150                 170
         .         .         .         .         .         .
TTCGTGACTCCCACGTCCTTCACAGCAGACTGAGCCAGTGCCCAGAGGTTCACCCTTTGC
 R  D  S  H  V  L  H  S  R  L  S  Q  C  P  E  V  H  P  L  P

       190                 210                 230
         .         .         .         .         .         .
CTACACCTGTCCTGCTGCCTGCTGTGGACTTTAGCTTGGGAGAATGGAAAACCCAGATGG
 T  P  V  L  L  P  A  V  D  F  S  L  G  E  W  K  T  Q  M  E

       250                 270                 290
         .         .         .         .         .         .
AGGAGACCAAGGCACAGGACATTCTGGGAGCAGTGACCCTTCTGCTGGAGGGAGTGATGG
 E  T  K  A  Q  D  I  L  G  A  V  T  L  L  L  E  G  V  M  A
```

FIG. 2A

```
           310                 330                 350
             .         .         .         .         .         .
CAGCACGGGGACAACTGGGACCCACTTGCCTCTCATCCCTCCTGGGGCAGCTTTCTGGAC
 A  R  G  Q  L  G  P  T  C  L  S  S  L  L  G  Q  L  S  G  Q

           370                 390                 410
             .         .         .         .         .         .
AGGTCCGTCTCCTCCTTGGGGCCCTGCAGAGCCTCCTTGGAACCCAGCTTCCTCCACAGG
 V  R  L  L  L  G  A  L  Q  S  L  L  G  T  Q  L  P  P  Q  G

           430                 450                 470
             .         .         .         .         .         .
GCAGGACCACAGCTCACAAGGATCCCAATGCCATCTTCCTGAGCTTCCAACACCTGCTCC
 R  T  T  A  H  K  D  P  N  A  I  F  L  S  F  Q  H  L  L  R

           490                 510                 530
             .         .         .         .         .         .
GAGGAAAGGTGCGTTTCCTGATGCTTGTAGGAGGGTCCACCCTCTGCGTCAGGCGGGCCC
 G  K  V  R  F  L  M  L  V  G  G  S  T  L  C  V  R  R  A  P

           550                 570                 590
             .         .         .         .         .         .
CACCCACCACAGCTGTCCCCAGCAGAACCTCTCTAGTCCTCACACTGAACGAGCTCTAGG
 P  T  T  A  V  P  S  R  T  S  L  V  L  T  L  N  E  L  *

TCGAC
```

FIG.2B

FIG.8A
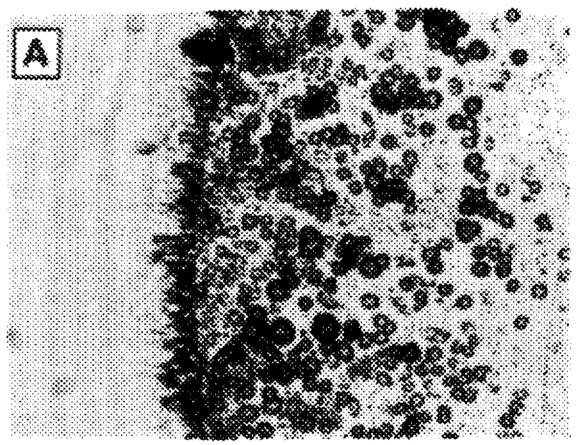
FIG.8B
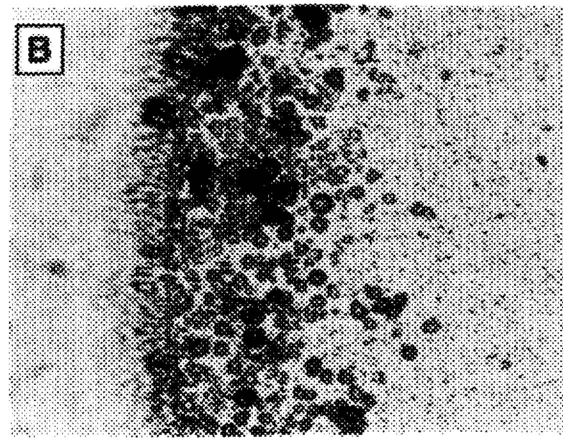
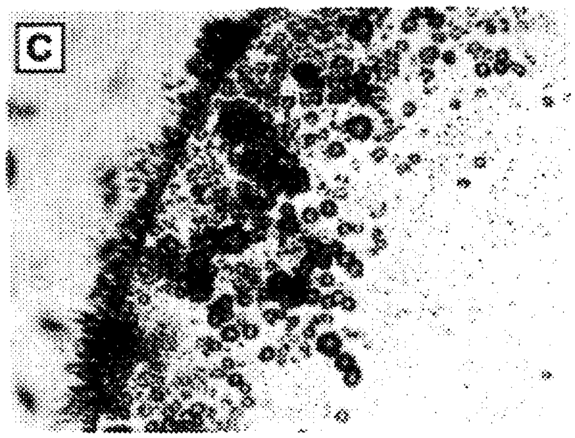
FIG.8C
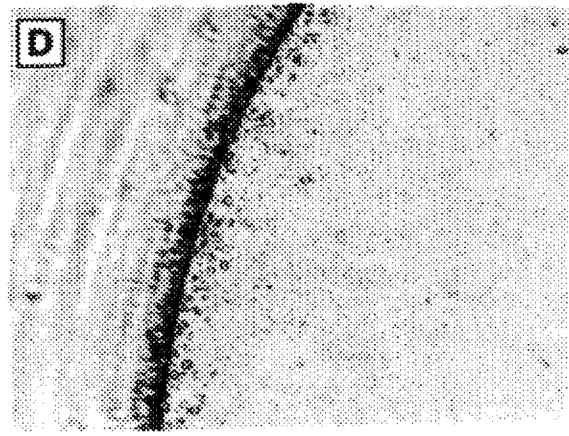
FIG.8D

SEQUENCE LISTING ( 1 ) GENERAL INFORMATION:

( i i i ) NUMBER OF SEQUENCES: 17

( 2 ) INFORMATION FOR SEQ ID NO:1:

( i ) SEQUENCE CHARACTERISTICS:
( A ) LENGTH: 1342 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 36..1094

( i x ) FEATURE:
( A ) NAME/KEY: mat_peptide
( B ) LOCATION: 99..1094

( i x ) FEATURE:
( A ) NAME/KEY: sig_peptide
( B ) LOCATION: 36..98

( x i ) SEQUENCE DESCRIPTION: SEQ ID NO:1:

```
CAGGGAGCCA CGCCAGCCAA GACACCCCGG CCAGA ATG GAG CTG ACT GAA TTG     53
                                       Met Glu Leu Thr Glu Leu
                                       -21 -20

CTC CTC GTG GTC ATG CTT CTC CTA ACT GCA AGG CTA ACG CTG TCC AGC    101
Leu Leu Val Val Met Leu Leu Leu Thr Ala Arg Leu Thr Leu Ser Ser
-15                 -10                 -5                    1

CCG GCT CCT CCT GCT TGT GAC CTC CGA GTC CTC AGT AAA CTG CTT CGT    149
Pro Ala Pro Pro Ala Cys Asp Leu Arg Val Leu Ser Lys Leu Leu Arg
                5                   10                  15

GAC TCC CAT GTC CTT CAC AGC AGA CTG AGC CAG TGC CCA GAG GTT CAC    197
Asp Ser His Val Leu His Ser Arg Leu Ser Gln Cys Pro Glu Val His
        20                  25                  30

CCT TTG CCT ACA CCT GTC CTG CTG CCT GCT GTG GAC TTT AGC TTG GGA    245
Pro Leu Pro Thr Pro Val Leu Leu Pro Ala Val Asp Phe Ser Leu Gly
    35                  40                  45

GAA TGG AAA ACC CAG ATG GAG GAG ACC AAG GCA CAG GAC ATT CTG GGA    293
Glu Trp Lys Thr Gln Met Glu Glu Thr Lys Ala Gln Asp Ile Leu Gly
50                  55                  60                  65

GCA GTG ACC CTT CTG CTG GAG GGA GTG ATG GCA GCA CGG GGA CAA CTG    341
Ala Val Thr Leu Leu Leu Glu Gly Val Met Ala Ala Arg Gly Gln Leu
                70                  75                  80

GGA CCC ACT TGC CTC TCA TCC CTC CTG GGG CAG CTT TCT GGA CAG GTC    389
Gly Pro Thr Cys Leu Ser Ser Leu Leu Gly Gln Leu Ser Gly Gln Val
            85                  90                  95

CGT CTC CTC CTT GGG GCC CTG CAG AGC CTC CTT GGA ACC CAG CTT CCT    437
Arg Leu Leu Leu Gly Ala Leu Gln Ser Leu Leu Gly Thr Gln Leu Pro
        100                 105                 110

CCA CAG GGC AGG ACC ACA GCT CAC AAG GAT CCC AAT GCC ATC TTC CTG    485
Pro Gln Gly Arg Thr Thr Ala His Lys Asp Pro Asn Ala Ile Phe Leu
    115                 120                 125

AGC TTC CAA CAC CTG CTC CGA GGA AAG GTG CGT TTC CTG ATG CTT GTA    533
Ser Phe Gln His Leu Leu Arg Gly Lys Val Arg Phe Leu Met Leu Val
130                 135                 140                 145

GGA GGG TCC ACC CTC TGC GTC AGG CGG GCC CCA CCC ACC ACA GCT GTC    581
Gly Gly Ser Thr Leu Cys Val Arg Arg Ala Pro Pro Thr Thr Ala Val
                150                 155                 160

CCC AGC AGA ACC TCT CTA GTC CTC ACA CTG AAC GAG CTC CCA AAC AGG    629
Pro Ser Arg Thr Ser Leu Val Leu Thr Leu Asn Glu Leu Pro Asn Arg
            165                 170                 175

ACT TCT GGA TTG TTG GAG ACA AAC TTC ACT GCC TCA GCC AGA ACT ACT    677
Thr Ser Gly Leu Leu Glu Thr Asn Phe Thr Ala Ser Ala Arg Thr Thr
        180                 185                 190

GGC TCT GGG CTT CTG AAG TGG CAG CAG GGA TTC AGA GCC AAG ATT CCT    725
Gly Ser Gly Leu Leu Lys Trp Gln Gln Gly Phe Arg Ala Lys Ile Pro
    195                 200                 205

GGT CTG CTG AAC CAA ACC TCC AGG TCC CTG GAC CAA ATC CCC GGA TAC    773
Gly Leu Leu Asn Gln Thr Ser Arg Ser Leu Asp Gln Ile Pro Gly Tyr
210                 215                 220                 225

CTG AAC AGG ATA CAC GAA CTC TTG AAT GGA ACT CGT GGA CTC TTT CCT    821
```

```
Leu Asn Arg Ile His Glu Leu Leu Asn Gly Thr Arg Gly Leu Phe Pro
                230                 235                 240

GGA CCC TCA CGC AGG ACC CTA GGA GCC CCG GAC ATT TCC TCA GGA ACA      869
Gly Pro Ser Arg Arg Thr Leu Gly Ala Pro Asp Ile Ser Ser Gly Thr
            245                 250                 255

TCA GAC ACA GGC TCC CTG CCA CCC AAC CTC CAG CCT GGA TAT TCT CCT      917
Ser Asp Thr Gly Ser Leu Pro Pro Asn Leu Gln Pro Gly Tyr Ser Pro
        260                 265                 270

TCC CCA ACC CAT CCT CCT ACT GGA CAG TAT ACG CTC TTC CCT CTT CCA      965
Ser Pro Thr His Pro Pro Thr Gly Gln Tyr Thr Leu Phe Pro Leu Pro
    275                 280                 285

CCC ACC TTG CCC ACC CCT GTG GTC CAG CTC CAC CCC CTG CTT CCT GAC     1013
Pro Thr Leu Pro Thr Pro Val Val Gln Leu His Pro Leu Leu Pro Asp
290                 295                 300                 305

CCT TCT GCT CCA ACG CCC ACC CCT ACC AGC CCT CTT CTA AAC ACA TCC     1061
Pro Ser Ala Pro Thr Pro Thr Pro Thr Ser Pro Leu Leu Asn Thr Ser
                310                 315                 320

TAC ACC CAC TCC CAG AAT CTG TCT CAG GAA GGG TAAGGTTCTC AGACACTGCC     1114
Tyr Thr His Ser Gln Asn Leu Ser Gln Glu Gly
            325                 330

GACATCAGCA TTGTCTCGTG TACAGCTCCC TTCCCTGCAG GGCGCCCCTG GGAGACAACT     1174

GGACAAGATT TCCTACTTTC TCCTGAAACC CAAAGCCCTG GTAAAAGGGA TACACAGGAC     1234

TGAAAAGGGA ATCATTTTTC ACTGTACATT ATAAACCTTC AGAAGCTATT TTTTTAAGCT     1294

ATCAGCAATA CTCATCAGAG CAGCTAGCTC TTTGGTCTAT TTTCTGCA                  1342
```

( 2 ) INFORMATION FOR SEQ ID NO:2:

( i ) SEQUENCE CHARACTERISTICS:
( A ) LENGTH: 353 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Glu Leu Thr Glu Leu Leu Leu Val Val Met Leu Leu Leu Thr Ala
-21 -20                 -15                 -10

Arg Leu Thr Leu Ser Ser Pro Ala Pro Pro Ala Cys Asp Leu Arg Val
 -5                       1               5                  10

Leu Ser Lys Leu Leu Arg Asp Ser His Val Leu His Ser Arg Leu Ser
             15                  20                  25

Gln Cys Pro Glu Val His Pro Leu Pro Thr Pro Val Leu Leu Pro Ala
         30                  35                  40

Val Asp Phe Ser Leu Gly Glu Trp Lys Thr Gln Met Glu Glu Thr Lys
     45                  50                  55

Ala Gln Asp Ile Leu Gly Ala Val Thr Leu Leu Leu Glu Gly Val Met
 60                  65                  70                  75

Ala Ala Arg Gly Gln Leu Gly Pro Thr Cys Leu Ser Ser Leu Leu Gly
                 80                  85                  90

Gln Leu Ser Gly Gln Val Arg Leu Leu Leu Gly Ala Leu Gln Ser Leu
             95                 100                 105

Leu Gly Thr Gln Leu Pro Pro Gln Gly Arg Thr Thr Ala His Lys Asp
        110                 115                 120

Pro Asn Ala Ile Phe Leu Ser Phe Gln His Leu Leu Arg Gly Lys Val
    125                 130                 135

Arg Phe Leu Met Leu Val Gly Gly Ser Thr Leu Cys Val Arg Arg Ala
140                 145                 150                 155
```

-continued

```
Pro Pro Thr Thr Ala Val Pro Ser Arg Thr Ser Leu Val Leu Thr Leu
                160                 165                 170

Asn Glu Leu Pro Asn Arg Thr Ser Gly Leu Leu Glu Thr Asn Phe Thr
            175                 180                 185

Ala Ser Ala Arg Thr Thr Gly Ser Gly Leu Leu Lys Trp Gln Gln Gly
        190                 195                 200

Phe Arg Ala Lys Ile Pro Gly Leu Leu Asn Gln Thr Ser Arg Ser Leu
    205                 210                 215

Asp Gln Ile Pro Gly Tyr Leu Asn Arg Ile His Glu Leu Leu Asn Gly
220                 225                 230                 235

Thr Arg Gly Leu Phe Pro Gly Pro Ser Arg Arg Thr Leu Gly Ala Pro
                240                 245                 250

Asp Ile Ser Ser Gly Thr Ser Asp Thr Gly Ser Leu Pro Pro Asn Leu
            255                 260                 265

Gln Pro Gly Tyr Ser Pro Ser Pro Thr His Pro Pro Thr Gly Gln Tyr
        270                 275                 280

Thr Leu Phe Pro Leu Pro Pro Thr Leu Pro Thr Pro Val Val Gln Leu
    285                 290                 295

His Pro Leu Leu Pro Asp Pro Ser Ala Pro Thr Pro Thr Pro Thr Ser
300                 305                 310                 315

Pro Leu Leu Asn Thr Ser Tyr Thr His Ser Gln Asn Leu Ser Gln Glu
                320                 325                 330

Gly
```

( 2 ) INFORMATION FOR SEQ ID NO:3:

( i ) SEQUENCE CHARACTERISTICS:
( A ) LENGTH: 605 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 12..596

( i x ) FEATURE:
( A ) NAME/KEY: mat_peptide
( B ) LOCATION: 75..596

( i x ) FEATURE:
( A ) NAME/KEY: sig_peptide
( B ) LOCATION: 12..74

( x i ) SEQUENCE DESCRIPTION: SEQ ID NO:3:

```
TCTAGACCAC C ATG GAG CTG ACT GAA TTG CTC CTC GTG GTC ATG CTT CTC      50
             Met Glu Leu Thr Glu Leu Leu Leu Val Val Met Leu Leu
             -21 -20                 -15                 -10

CTA ACT GCA AGG CTA ACG CTG TCC AGC CCG GCT CCT CCT GCT TGT GAC      98
Leu Thr Ala Arg Leu Thr Leu Ser Ser Pro Ala Pro Pro Ala Cys Asp
             -5                   1               5

CTC CGA GTC CTC AGT AAA CTG CTT CGT GAC TCC CAC GTC CTT CAC AGC     146
Leu Arg Val Leu Ser Lys Leu Leu Arg Asp Ser His Val Leu His Ser
     10                  15                  20

AGA CTG AGC CAG TGC CCA GAG GTT CAC CCT TTG CCT ACA CCT GTC CTG     194
Arg Leu Ser Gln Cys Pro Glu Val His Pro Leu Pro Thr Pro Val Leu
 25                  30                  35                  40

CTG CCT GCT GTG GAC TTT AGC TTG GGA GAA TGG AAA ACC CAG ATG GAG     242
Leu Pro Ala Val Asp Phe Ser Leu Gly Glu Trp Lys Thr Gln Met Glu
                 45                  50                  55
```

-continued

```
GAG ACC AAG GCA CAG GAC ATT CTG GGA GCA GTG ACC CTT CTG CTG GAG        290
Glu Thr Lys Ala Gln Asp Ile Leu Gly Ala Val Thr Leu Leu Leu Glu
             60                  65                  70

GGA GTG ATG GCA GCA CGG GGA CAA CTG GGA CCC ACT TGC CTC TCA TCC        338
Gly Val Met Ala Ala Arg Gly Gln Leu Gly Pro Thr Cys Leu Ser Ser
         75                  80                  85

CTC CTG GGG CAG CTT TCT GGA CAG GTC CGT CTC CTC CTT GGG GCC CTG        386
Leu Leu Gly Gln Leu Ser Gly Gln Val Arg Leu Leu Leu Gly Ala Leu
     90                  95                 100

CAG AGC CTC CTT GGA ACC CAG CTT CCT CCA CAG GGC AGG ACC ACA GCT        434
Gln Ser Leu Leu Gly Thr Gln Leu Pro Pro Gln Gly Arg Thr Thr Ala
105                 110                 115                 120

CAC AAG GAT CCC AAT GCC ATC TTC CTG AGC TTC CAA CAC CTG CTC CGA        482
His Lys Asp Pro Asn Ala Ile Phe Leu Ser Phe Gln His Leu Leu Arg
            125                 130                 135

GGA AAG GTG CGT TTC CTG ATG CTT GTA GGA GGG TCC ACC CTC TGC GTC        530
Gly Lys Val Arg Phe Leu Met Leu Val Gly Gly Ser Thr Leu Cys Val
        140                 145                 150

AGG CGG GCC CCA CCC ACC ACA GCT GTC CCC AGC AGA ACC TCT CTA GTC        578
Arg Arg Ala Pro Pro Thr Thr Ala Val Pro Ser Arg Thr Ser Leu Val
    155                 160                 165

CTC ACA CTG AAC GAG CTC TAGGTCGAC                                      605
Leu Thr Leu Asn Glu Leu
    170
```

( 2 ) INFORMATION FOR SEQ ID NO:4:

( i ) SEQUENCE CHARACTERISTICS:
( A ) LENGTH: 195 amino acids
( B ) TYPE: amino acid
( D ) TOPOLOGY: linear ( i i ) MOLECULE TYPE: protein ( x i ) SEQUENCE DESCRIPTION: SEQ ID NO:4:

```
Met Glu Leu Thr Glu Leu Leu Leu Val Val Met Leu Leu Leu Thr Ala
-21 -20                 -15                 -10

Arg Leu Thr Leu Ser Ser Pro Ala Pro Pro Ala Cys Asp Leu Arg Val
 -5                   1               5                  10

Leu Ser Lys Leu Leu Arg Asp Ser His Val Leu His Ser Arg Leu Ser
             15                  20                  25

Gln Cys Pro Glu Val His Pro Leu Pro Thr Pro Val Leu Leu Pro Ala
         30                  35                  40

Val Asp Phe Ser Leu Gly Glu Trp Lys Thr Gln Met Glu Glu Thr Lys
     45                  50                  55

Ala Gln Asp Ile Leu Gly Ala Val Thr Leu Leu Leu Glu Gly Val Met
 60                  65                  70                  75

Ala Ala Arg Gly Gln Leu Gly Pro Thr Cys Leu Ser Ser Leu Leu Gly
                 80                  85                  90

Gln Leu Ser Gly Gln Val Arg Leu Leu Leu Gly Ala Leu Gln Ser Leu
             95                 100                 105

Leu Gly Thr Gln Leu Pro Pro Gln Gly Arg Thr Thr Ala His Lys Asp
        110                 115                 120

Pro Asn Ala Ile Phe Leu Ser Phe Gln His Leu Leu Arg Gly Lys Val
    125                 130                 135

Arg Phe Leu Met Leu Val Gly Gly Ser Thr Leu Cys Val Arg Arg Ala
140                 145                 150                 155

Pro Pro Thr Thr Ala Val Pro Ser Arg Thr Ser Leu Val Leu Thr Leu
                160                 165                 170
```

Asn Glu Leu ( 2 ) INFORMATION FOR SEQ ID NO:5:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:5:

CCCATGTCAA TCACAGCAGA CT 22

( 2 ) INFORMATION FOR SEQ ID NO:6:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:6:

CTTCACAGCA ACCTGAGCCA GT 22

( 2 ) INFORMATION FOR SEQ ID NO:7:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:7:

CAGTGCAACG AGACCCACCC TTTG 24

( 2 ) INFORMATION FOR SEQ ID NO:8:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:8:

GCCTACAAAT GTCACGCTGC CTGCT 25

( 2 ) INFORMATION FOR SEQ ID NO:9:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:9:

CCCACTTGTA ACTCATCCCT C 21

( 2 ) INFORMATION FOR SEQ ID NO:10:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:10:

CAACTGAACG CCACTTGTCT CTCA 24

( 2 ) INFORMATION FOR SEQ ID NO:11:

( i ) SEQUENCE CHARACTERISTICS:
( A ) LENGTH: 26 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:11:

ACTTGTCTCA ACTCCACCCT GGGGGA 26

( 2 ) INFORMATION FOR SEQ ID NO:12:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:12:

CTCCTGGGGA ACCTTTCTGG A 21

( 2 ) INFORMATION FOR SEQ ID NO:13:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:13:

GACCACAAAT CACACCGATC CCAAT 25

( 2 ) INFORMATION FOR SEQ ID NO:14:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:14:

ACCCTTTGTC TACAAATGTC ACGCTGCCTG CT 32

( 2 ) INFORMATION FOR SEQ ID NO:15:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear -continued ( i i ) MOLECULE TYPE: cDNA ( x i ) SEQUENCE DESCRIPTION: SEQ ID NO:15:

TCTCTCAAAC CTCACGGGGG AGCTT 25

( 2 ) INFORMATION FOR SEQ ID NO:16:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:16:

TGGAAAAATC AGACGGAGGA GAC 23

( 2 ) INFORMATION FOR SEQ ID NO:17:

( i ) SEQUENCE CHARACTERISTICS:
( A ) LENGTH: 25 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:17:

TGGAGGAGAA CAAGACACAG GACAT 25

DNA ENCODING MEGAKARYOCYTE GROWTH AND DEVELOPMENT FACTOR ANALOGS

FIELD OF THE INVENTION

The present invention relates to MGDF analogs having at least one changed O- or N-linked glycosylation site. The invention also relates to DNA sequences encoding these MGDF analogs, and recombinant plasmids and host cells for analog expression.

BACKGROUND OF THE INVENTION

MGDF, or megakaryocyte growth and differentiation factor, is a recently cloned cytokine that appears to be the major regulator of circulating platelet levels. See Bartley, T. D. et al., *Cell* 77:1117–1124 (1994); Lok, S. et al., *Nature* 369:565–568 (1994); de Sauvage, F. J. et al., *Nature* 369:533–538 (1994); Miyazake, H. et al., *Exp. Hematol.* 22:838 (1994); and Kuter, D. J. et al., *PNAS USA*, 91:11104–11108 (1994). MGDF is also referred to as thrombopoietin (TPO), mpl-ligand, and megapoietin. Mature human MGDF is a protein having 332 amino acids in total. The sequence of this protein and the corresponding cDNA are shown in FIG. 1 herein (SEQ. ID NOS.: 1 and 2).

Recombinant MGDF produced in both Chinese Hamster Ovary (CHO) and *E. coli* cells has been demonstrated to have a biological activity of specifically stimulating or increasing megakaryocytes and/or platelets in vivo in mice, rats and monkeys. See e.g., Hunt, P. et al., *Blood* 84(10) :390A (1994). Human MGDF molecules that have been truncated so that they extend at least 151 amino acids, starting from amino acid position 1 in FIG. 1, retain biological activity in vivo. FIG. 2 (SEQ. ID NOS.:3 and 4) shows one example of a truncated MGDF molecule having 174 amino acids that has biological activity and was used to create MGDF analogs in the examples section below. It is also possible to remove up to the first six amino acids at the N-terminus of the human sequence MGDF protein and retain biological activity. Therefore, it appears that biological activity is retained within amino acids 7 to 151 (inclusive) of the mature amino acid sequence of human MGDF shown in FIG. 1.

In general, many cell surface and secretory proteins produced by eucaryotic cells are modified with one or more oligosaccharide groups. This modification, referred to as glycosylation, can dramatically affect the physical properties of proteins and can also be important in protein stability, secretion, and subcellular localization. Proper glycosylation can be essential for biological activity. In fact, some genes from eucaryotic organisms, when expressed in bacteria (e.g., *E. coli*) which lack cellular processes for glycosylating proteins, yield proteins that are recovered with little or no activity by virtue of their lack of glycosylation.

Glycosylation occurs at specific locations or sites along the polypeptide backbone and is usually of two types: O-linked oligosaccharides are attached to serine (Ser) or threonine (Thr) residues while N-linked oligosaccharides (chains) are attached to asparagine residues when they are part of the sequence Asn-X-Ser/Thr, where X can be any amino acid except proline. X is preferably one of the 20 naturally occurring amino acids other than proline. The structures of N-linked and O-linked oligosaccharides and the sugar residues found in each type are different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein.

As used herein glycosylation "sites" are amino acid residues that are structurally able to link to glycosyl residues, although such sites may or may not be actually linked to a glycosyl residue. As noted above, O-linked sites are either Ser or Thr residues, whereas N-linked sites are either Asn-X-Ser or Asn-X-Thr, where X is defined as any amino acid other than Pro. Whether a given site is glycosylated with a glycosyl chain is determined by the host cell in which the molecule is expressed, the amino acids neighboring the site, and other factors. As used herein, the number of "chains" attached to a given MGDF analog will be the average number of carbohydrate (i.e., glycosyl) chains attached to a given MGDF molecule expressed by a particular host cell. Notably, the glycosylation sites for natural and corresponding recombinant MGDF will generally be the same, whereas the number of chains will possibly vary depending upon whether the particular host cell used for recombinant expression attaches glycosyl chains to the same sites or not, as compared to the natural source. Herein, whenever a comparison is made between recombinant and natural MGDF analogs, the same number of amino acids will be compared, regardless of whether the natural source actually produces an MGDF molecule having that length. Thus, "natural" refers to the sequence employed in a particular species (such as human) rather than the length of the molecule actually expressed in such natural source.

Naturally occuring MGDF is a glycosylated molecule. The glycosylation pattern of natural MGDF is related to two key domains that have been found in MGDF. The sequence of the first approximately 151 amino acids of human MGDF, corresponding to an active portion of the molecule, bears notable homology to erythropoietin (EPO), a cytokine capable of stimulating production of erythrocytes, and is referred to as the "EPO-like" domain of human MGDF. The remaining amino acids of the mature protein make up a so-called "N-linked carbohydrate" domain, since they include most if not all of the sites for N-linked glycosylation. In human MGDF, there are six N-linked glycosylation sites all contained in the N-linked glycosylation domain. Both domains contain O-linked glycosylation sites. There are an estimated 12–14 O-linked glycosylation chains in the molecule. Experimental evidence with human MGDF DNA expressed recombinantly in CHO cells reveals that in the EPO-like domain at least two O-linked sites are glycosylated, at positions 1 (Ser) and 37 (Thr).

Glycoproteins such as MGDF can be separated into different charged forms using techniques such as isoelectric focusing (IEF). For example, several parties have reported IEF studies of crude and partially purified erythropoietin preparations (Lukowsky et al., *J. Biochem.* 50:909 (1972); Shelton et al., *Biochem. Med.* 12:45 (1975); Fuhr et al., *Biochem. Biophys. Res. Comm.* 98:930 (1981)).

In spite of the above information on glyscosylation of MGDF molecules, there remains a need to obtain MGDF molecules having a different glycosylation pattern and which retain or have improved biological activity.

Accordingly, it is an object of the present invention to provide novel glycosylated MGDF molecules. It is a further object of this invention to provide pharmaceutical compositions containing such molecules and methods of treating conditions treatable by MGDF with the MGDF analogs of this invention.

SUMMARY OF THE INVENTION

In one embodiment, the subject invention relates to analogs of MGDF comprising an amino acid sequence which includes at least one added, at least one deleted, and/or a combination of at least one added and deleted, site for glycosylation as compared to the corresponding natural sequence MGDF. The added or deleted site(s) for glycosylation may result in a greater or lesser number of carbohydrate chains, and higher or lower sialic acid content, than corresponding natural sequence MGDF, particularly human MGDF. For example, one type of analog could involve deleting one or more N- or O-linked sites, and addition of one or more N- or O-linked sites at the same or another position.

In another aspect of the above embodiment, the subject invention relates to MGDF analogs comprising amino acid sequences which involve replacement of one or more N- or O-linked glycosylation sites with one or more non-naturally occurring sites. Thus, an N-linked site may be replaced with a different N-linked site; an N-linked site may be replaced with an O-linked site; an O-linked site may be replaced with a different O-linked site; and an O-linked site may be replaced with an N-linked site.

Combinations of any of the above changes are further encompassed within this invention.

The invention further encompasses DNA sequences encoding such MGDF analogs, and recombinant plasmids and host cells for analog expression.

In all of the above cases, it is preferred that the change in glycosylation site result in a change in the number, location or type (N- vs. O-) of glycosyl chains in the resulting MGDF analog and retains a biological activity of MGDF.

BRIEF DESCRIPTION OF THE DRAWINGS

FIG. 1 shows the DNA and amino acid sequence of human MGDF including a signal peptide (amino acids −21 to −1) and the mature amino acid sequence (1-332).

FIG. 2 shows the DNA and amino acid sequence of MGDF corresponding to amino acids 1-174 of the human mature MGDF sequence. The sequences flanking the coding regions have introduced XbaI and SalI cloning sites at the 5' and 3' ends respectively.

FIG. 8 shows the results of a human megakaryocyte growth bioassay with MGDF analogs. Panels A and D are the positive and negative controls respectively. The well pictured in panel A received 37.5 pg of wild type (i.e., natural sequence) MGDF 1-174 COS-1 conditioned medium and shows substantial megakaryocyte growth. Panel D received 1.5 ul of COS-1 mock conditioned medium and shows no growth. Panels B and C are MGDF 1-174 analogs 7 and 10 respectively. Panel B received 9.0 pg of MGDF COS-1 conditioned medium while panel C received 27 pg and both show excellent megakaryocyte growth.

DETAILED DESCRIPTION OF THE INVENTION

Figure 3:
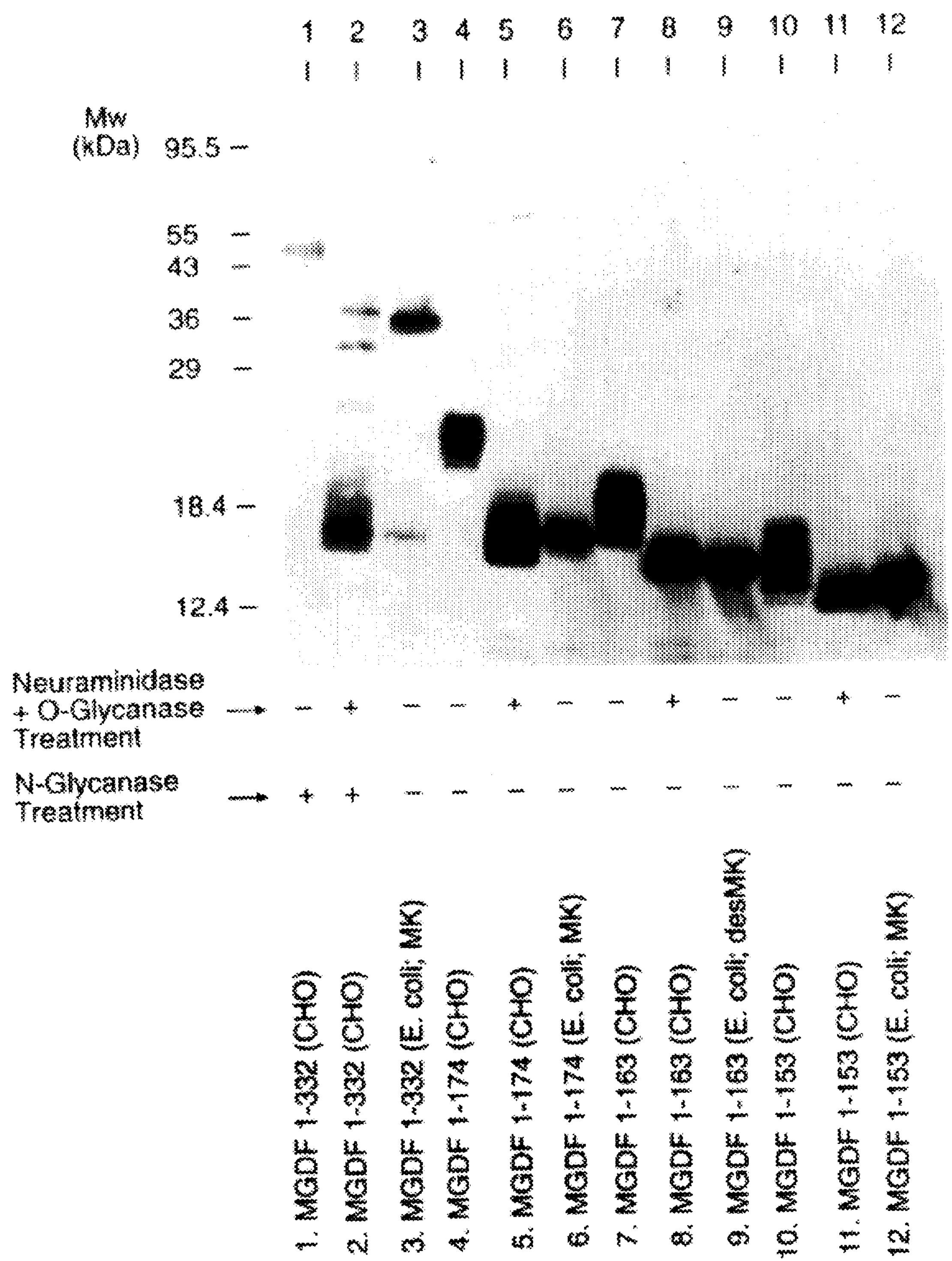
FIG. 3 shows a Western blot with *E. coli* and CHO MGDF. MK stands for Met-Lys, which is added to the N-terminus of MGDF for expression, and may be cleaved off using a dipeptidase, such as cathepsin C. A molecule in which MK has been removed is referred to as desMK. Treatment with the glycosidases neuraminidase and O-glycanase is indicated.

The subject invention provides MGDF with different glycosylation sites as compared to natural MGDF having a corresponding sequence.

In a first embodiment, the subject invention relates to analogs of MGDF comprising an amino acid sequence which includes at least one added, at least one deleted, and/or at least one added and deleted, site for glycosylation as compared to corresponding natural sequence MGDF. The added or deleted site(s) for glycosylation may result in a greater or lesser number of carbohydrate chains, and higher or lower sialic acid content, than corresponding natural sequence MGDF, particularly human MGDF. A combination of a deletion of one site and addition of another site would result in no net change in the number of sites, but rather, a change in location and/or type of site. Such combined change analogs are also encompassed within this invention.

In a another aspect of the above embodiment, the subject invention relates to MGDF analogs comprising amino acid sequences which include replacement of one or more N- or O-linked glycosylation sites with one or more non-naturally occurring sites. Thus, an N-linked site may be replaced with a different N-linked site; an N-linked site may be replaced with an O-linked site; an O-linked site may be replaced with a different O-linked site; and/or an O-linked site may be replaced with an N-linked site.

The term "MGDF", as used herein, includes naturally occurring MGDF, truncations of naturally occurring MGDF as well as non-naturally occurring polypeptides having an amino acid sequence and glycosylation sufficiently duplicative of that of naturally occurring MGDF to allow possession of a biological activity of specifically stimulating growth, development and/or production of megakaryocytes and/or platelets.

In a preferred embodiment, MGDF is the product of the expression of an exogenous DNA sequence that has been transfected into a eukaryotic host cell; that is, in a preferred embodiment the MGDF is "recombinant MGDF". The preferred eucaryotic host is mammalian, particularly preferably CHO cells. Recombinant MGDF is advantageously produced according to the procedures described herein and in the publications cited herein regarding cloning and expression of MGDF.

Some additional preferred MGDF molecules have the following amino acid sequences, based on FIG. 1 herein:

MGDF 1-332 amino acids 1-332 of FIG. 1

MGDF 1-191 amino acids 1-191 of FIG. 1

MGDF 1-183 amino acids 1-183 of FIG. 1

MGDF 1-174 amino acids 1-174 of FIG. 1
MGDF 1-163 amino acids 1-163 of FIG. 1
MGDF 1-153 amino acids 1-153 of FIG. 1
MGDF 1-152 amino acids 1-152 of FIG. 1
MGDF 1-151 amino acids 1-151 of FIG. 1
MGDF 7-332 amino acids 7-332 of FIG. 1
MGDF 7-191 amino acids 7-191 of FIG. 1
MGDF 7-183 amino acids 7-183 of FIG. 1
MGDF 7-174 amino acids 7-174 of FIG. 1
MGDF 7-163 amino acids 7-163 of FIG. 1
MGDF 7-153 amino acids 7-153 of FIG. 1
MGDF 7-152 amino acids 7-152 of FIG. 1
MGDF 7-151 amino acids 7-151 of FIG. 1

It should be noted that MGDF 1-183, 1-191, 7-183, and 7-191 encompass one or two additional naturally-occuring glycosylation sites on the C-terminus thereof, as compared to shorter sequences. In each of the above cases, Met-Lys may further be included in the N-terminus thereof.

The in vitro specific activities referred to herein are measurements of relative in vitro specific activities and are not measurements of absolute in vitro specific activities. For the purposes of this application, the specific activities are used only to compare relative activities of MGDF analogs that have been assayed using the same assay, using the same conditions including the same internal standard, and having the same analysis of the data used to calculate specific activity, etc.

As used herein the phrase "analog of MGDF" refers to MGDF with one or more changes in the amino acid sequence of MGDF which result in a change in the type (N- or O-linked), number, or location of sites for carbohydrate attachment. In a preferred embodiment, the change in glycosylation site(s) results in a change in the number of glycosyl chains attached to the MGDF molecule. In a particularly preferred embodiment, the change in glycosylation site(s) adds at least one (generally 1–6, preferably 1–5, particularly preferably 1–3) glycosyl chains, and most preferably the chain(s) is(are) added via N-linkage. In another particularly preferred embodiment, the MGDF analog retains at least equivalent biological activity as compared to natural sequence MGDF (e.g., human MGDF) and may possess substantially higher activity, as measured in assays for biological activity.

To prepare such analogs of MGDF, preferably they are generated by site-directed mutagenesis resulting in additions, deletions, or substitutions of amino acid residues that add, eliminate or alter sites that are available for glycosylation. By "altered" is meant that a site has been deleted while another has been added at the same or another location as the deleted site. However, as is appreciated by those skilled in the art, other methods could result in a gene encoding same amino acid sequence, and such methods are encompassed herein. The resulting analogs may have fewer or more (preferably more) carbohydrate chains than natural human/recombinant MGDF.

Addition of one or more carbohydrate (i.e., glycosyl) chains to MGDF is one important object of this invention. MGDF analogs having more carbohydrate chains than those found in the corresponding naturally-occurring amino acid sequence (e.g., 1-332 or 1-174, etc.) are generated by adding glycosylation sites which do not perturb the secondary or tertiary conformation in a way that would substantially reduce biological activity. As used herein the "naturally-occurring" MGDF refers to an amino acid sequence having the corresponding number of amino acids as the relevent analog, even if the particular length of MGDF species is not actually expressed in the native species. Advantageously, the analog of MGDF has up to 6 additional sites for N-glycosylation or O-glycosylation, resulting in the addition of up to 6 additional N-linked or O-linked carbohydrate chains.

For example, a Pro at position 30 is replaced by an Asn and a Val at position 32 is replaced by a Thr to give the sequence Asn-Glu-Thr, which serves as a new site for N-glycosylation (analog 4 below; see Table 1). Analogs may also be constructed which have two or more additional N-linked chains by combining mutations; for example, analogs 4 and 10 described in Table 1 may be combined to yield an analog with two additional sites for carbohydrate addition (i.e., analog N15 in Table 1). In a like manner analogs with three or more added chains can be constructed. As will be appreciated by those skilled in the art, the subject invention includes many other analogs of MGDF having different sites for glycosylation (in terms of number, type or location of site). The MGDF analogs of this invention are in all cases particularly preferably based on MGDF having a human amino acid sequence (see FIGS. 1 and 2); however, analogs based on MGDF sequences from other species (e.g., dog, pig, monkey, mouse or rat) are also contemplated herein.

Also included within the analogs of this invention are analogs which have one or more amino acids extending from the carboxy terminal end of MGDF wherein the carboxy terminal extension provides at least one additional carbohydrate site. The carboxy terminus of MGDF will vary depending upon the particular form of MGDF used (e.g., MGDF 1-332 amino acids, or MGDF 1-163 amino acids). An additional carbohydrate site may be added to the carboxy terminus of an MGDF species by adding amino acids to the carboxy terminus, such amino acids containing one or more N- or O-linked glycosylation sites.

Table 1 lists some exemplary MGDF analogs which have additional sites for N-linked carbohydrate chains. The analogs have the sequence Asn-X-Ser or Asn-X-Thr included at various positions in the human MGDF polypeptide chain based on the human amino acid sequences to create N-linked sites. Table 1 also lists those analogs which add at least one additional N-linked carbohydrate chain, as evidenced by the migration of the glycoproteins on SDS gels (see, Example 6).

Also encompassed by the present invention are DNA sequences encoding the MGDF analogs disclosed herein, preferably those encoding analogs having additional sites for N-linked chains. Procedures used to introduce changes into the MGDF DNA sequence for the purpose of creating, deleting and/or altering attachment sites for carbohydrates are disclosed in Example 4.

These MGDF analogs can be the product of expression of an exogenous DNA sequence, i.e., produced through recombinant DNA technology, they can be chemically synthesized products or they may be produced by combined methods. An exogenous DNA sequence comprises cDNA, genomic DNA or chemically synthesized DNA encoding an MGDF analog. Recombinant DNA plasmids and eucaryotic host cells useful for the expression of said analogs are also provided. Expression vectors include any vector which is capable of expressing cloned DNA sequences in a eucaryotic host cell, particularly those vectors used for expression in COS and CHO cells. Examples of such vectors include plasmids pDSRα and pDSRα2, see *Mol. Cell. Biol.* 8:466–472 (1988); WO 91/13160 (1991); and WO 90/14363 (1990). The cultivation of COS and CHO host cells expressing MGDF analogs was carried out using standard procedures known to those skilled in the art.

Changing the number, type or location of carbohydrate chains attached to MGDF may confer advantageous properties such as increased solubility, greater resistance to proteolysis, reduced immunogenicity, increased serum half-life, and increased biological activity.

Conditioned media from COS cells expressing MGDF analogs N2–N15 (N1 is human MGDF 1-174; see FIG. 2) were analyzed for in vitro biological activity and the results shown in Table 4.

Another embodiment of the invention relates to mammalian (e.g., Chinese Hamster Ovary, CHO) host cells which preferentially synthesize MGDF or analogs of MGDF having greater than a specific number of sialic acids per molecule, e.g. greater than that found in MGDF 1-332, 1-174, 1-163, or 1-151 produced naturally or recombinantly in a eucaryotic cell.

The sialic acid content of the MGDF molecule may affect its in vivo biological activity. For example, tetraantennary (four-branched) N-linked oligosaccharides most commonly provide four possible sites for sialic acid attachment while bi- and triantennary oligosaccharides, which can substitute for the tetraantennary form at asparagine-linked sites, commonly have at most only two or three sialic acids attached. O-linked oligosaccharides commonly provide two sites for sialic acid attachment. Thus, MGDF molecules with N-linked carbohydrate substituted for O-linked carbohydrate can accommodate two additional sialic acids per chain provided the N-linked oligosaccharides are tetraantennary. Mammalian cell cultures are screened for those cells that preferentially add tetraantennary chains to recombinant MGDF, thereby maximizing the number of sites for sialic acid attachment.

Dihydrofolate reductase (DHFR) deficient Chinese Hamster Ovary (CHO) cells are a commonly used host cell for the production of recombinant glycoproteins including recombinant MGDF.

Compositions comprising a therapeutically effective amount of an MGDF analog in accordance with this together with a suitable diluent, adjuvant and/or carrier useful in MGDF therapy are further encompassed by this invention. A "therapeutically effective amount" as used herein refers to that amount which provides therapeutic effect for a given condition and administration regimen.

The present compositions can be systemically administered parenterally. Alternatively, the compositions may be administered intravenously or subcutaneously. When systemically administered, the therapeutic compositions for use in this invention may be in the form of a pyrogen-free, parenterally acceptable aqueous solution. The preparation of such pharmaceutically acceptable protein solutions, with due regard to pH, isotonicity, stability and the like, is within the skill of the art. The specific route chosen will depend upon the condition being treated. The administration of MGDF or MGDF analogs is preferably done as part of a formulation containing a suitable carrier, such as human serum albumin, a suitable diluent, such as a buffered saline solution, and/or a suitable adjuvant. The required dosage will be in amounts sufficient to raise the platelet levels of patients and will vary depending upon the severity of the condition being treated, the method of administration used and the like.

The conditions to be treated by the methods and compositions of the present invention are generally those which involve an existing megakaryocyte/platelet deficiency or an expected megakaryocyte/platelet deficiency in the future (e.g., because of planned surgery). Such conditions will usually be the result of a deficiency (temporary or permanent) of active MGDF in vivo. The generic term for platelet deficiency is thrombocytopenia, and hence the methods and compositions of the present invention are generally available for treating thrombocytopenia.

Thrombocytopenia (platelet deficiencies) may be present for various reasons, including chemotherapy and other therapy with a variety of drugs, radiation therapy, surgery, accidental blood loss, and other specific disease conditions. Exemplary specific disease conditions that involve thrombocytopenia and may be treated in accordance with this invention are: aplastic anemia, idiopathic thrombocytopenia, metastatic tumors which result in thrombocytopenia, systemic lupus erythematosus, splenomegaly, Fanconi's syndrome, vitamin B12 deficiency, folic acid deficiency, May-Hegglin anomaly, Wiskott-Aldrich syndrome, and paroxysmal nocturnal hemoglobinuria. Also, certain treatments for AIDS result in thrombocytopenia (e.g., AZT). Certain wound healing disorders might also benefit from an increase in platelet numbers.

With regard to anticipated platelet deficiencies, e.g., due to future surgery, an MGDF analog of the present invention could be administered several days to several hours prior to the need for platelets. With regard to acute situations, e.g., accidental and massive blood loss, an MGDF analog could be administered along with blood or purified platelets.

The dosage regimen involved in a method for treating the above-described conditions will be determined by the attending physician, considering various factors which modify the action of drugs, e.g. the age, condition, body weight, sex and diet of the patient, the severity of any infection, time of administration and other clinical factors. Generally, the daily regimen should be in the range of 0.01–1000 micrograms of MGDF analog per kilogram of body weight.

The therapeutic methods, compositions and polypeptides of the present invention may also be employed, alone or in combination with other cytokines, soluble Mpl (i.e., MGDF) receptor, hematopoietic factors, interleukins, growth factors or antibodies in the treatment of disease states characterized by other symptoms as well as platelet deficiencies. It is anticipated that an MGDF analog molecule will prove useful in treating some forms of thrombocytopenia in combination with general stimulators of hematopoiesis, such as IL-3 or GM-CSF. Other megakaryocytic stimulatory factors, i.e., meg-CSF, stem cell factor (SCF), leukemia inhibitory factor (LIF), oncostatin M (OSM), or other molecules with megakaryocyte stimulating activity may also be employed with MGDF. Additional exemplary cytokines or hematopoietic factors for such co-administration include IL-1 alpha, IL-1 beta, IL-2, IL-3, IL-4, IL-5, IL-6, IL-11, colony stimulating factor-1 (CSF-1), GM-CSF, granulocyte colony stimulating factor (G-CSF), EPO, interferon-alpha (IFN-alpha), IFN-beta, or IFN-gamma. It may further be useful to administer, either simultaneously or sequentially, an effective amount of a soluble mammalian Mpl receptor, which appears to have an effect of causing megakaryocytes to fragment into platelets once the megakaryocytes have reached mature form. Thus, administration of MGDF analog (to enhance the number of mature megakaryocytes) followed by administration of the soluble Mpl receptor (to inactivate the analog and allow the mature megakaryocytes to produce platelets) is expected to be a particularly effective means of stimulating platelet production. The dosage recited above would be adjusted to compensate for such additional components in the therapeutic composition. Progress of the treated patient can be monitored by conventional methods.

Additional modifications of the analogs of this invention may also be carried out, e.g., to increase activity, stability, half-life, etc. For example, pegylation (poly- or mono-) could be added to the MGDF analog.

The following examples are offered to more fully illustrate the invention, but are not to be construed as limiting the scope thereof. The MGDF standard used in the bioassays employed in the Examples is a recombinant MGDF standard that was expressed in *E. coli*, refolded into an active conformation and purified. Thus, only relative specific activities are being measured.

EXAMPLE 1

Construction of MGDF 1-174

Human MGDF gene encoding amino acids 1-174 of FIG. 2 was generated from a human fetal liver cDNA library (Bartley et al, *Cell* 77: 1117–1124 (1994) by polymerase chain reaction (PCR). The 5' PCR primer encoded the amino terminus of human MGDF, an XbaI site, and an optimized Kozak sequence. The 3' primer contained a termination codon and a SalI restriction site. The amplified DNA fragment was digested with XbaI and SalI then ligated to XbaI and SalI cut pDSRα2. The resultant plasmid, pDSRα2 MGDF 1-174 was used for mammalian cell expression. The sequence of the resulting gene is shown in FIG. 2.

Plasmid DNA containing MGDF 1-174 was digested with XbaI and SalI restriction enzymes, the resulting DNA fragments were subjected to agarose gel electrophoresis, and the 605 nt MGDF 1-174 DNA fragment was isolated from the gel using a GeneClean™ kit and procedures supplied by the manufacturer (BIO 101, Inc.). Plasmid pDSRα2 as described in WO 90/14363 (1990) was also digested with XbaI and SalI restriction enzymes and the nt vector fragment was recovered. Ligation of the two fragments results in pDSRα2 (MGDF 1-174).

EXAMPLE 2

Expression of MGDF 1-174 in CHO Cells and Purification

Dihydrofolate reductase deficient ($DHFR^-$) Chinese Hamster Ovary (CHO) cells were transfected with pDSRα2-MGDF 1-174. A 100 mm tissue culture dish was plated with $1\times10^6$ CHO $DHFR^-$ cells grown in CHO $D^-$ medium (DMEM, 10% Fetal bovine serum, 1% penicillin/streptomycin/glutamine, 1% nonessential amino acids (Gibco) and 1% HT supplement (Gibco)) the day before transfection. Four transfections were performed. For each transfection, plasmid DNA (50 μg) was linearized by digesting with Pvu I and Buffer H (Boehringer Mannheim). A DNA precipitate was then formed and added to the plates dropwise as per the Mammalian Cell Transfection Kit (Speciality Media). After 24 hours in a tissue culture incubator the medium was replaced with fresh CHO D– medium. Twenty four hours later the cells were split into 96 well tissue culture plates with 100 ul of CHO select medium (D-MEM, 5% dialyzed fetal Bovine serum, 1% penicillin/streptomycin/glutamine, 1% nonessential amino acids (Gibco)) per well and transformants were selected. Medium was changed weekly until colonies appeared. After two weeks, MGDF expression was screened for using the 32D cell proliferation assay described below (see Example 9). Those clones expressing in excess of $1\times10^5$ units/ml were expanded and frozen in cryogenic storage. One clone was expanded for roller bottle production and approximately 8 liters of conditioned medium was produced.

Plasmid pDSRα2 containing MGDF 1-174 cDNA was transfected into DHFR-deficient CHO cells as explained above. Two liters of serum-free CHO cell conditioned medium (50% D-MEM, 50% HAMS-F12, 1% penicillin/streptomycin/glutamine, 1% nonessential amino acids (Gibco)) from roller bottles seeded with CHO cells expressing MGDF 1-174 was concentrated 15 fold using a 2 L Amicon Model 2000 stirred cell and a 10,000 dalton molecular weight cut-off membrane (YM10, Amicon). Forty-five milliliters of concentrated conditioned medium was then loaded directly onto a 4 ml hu-MPL-X affinity column at a flow rate of 0.4 ml/min using a Pharmacia FPLC. The affinity column was constructed by coupling 1.5–2.5 milligrams of Mpl-X (the soluble extra-cellular domain of the Mpl receptor) per milliliter of Pharmacia CNBR activated Sepharose resin as recommended by the manufacturer. After loading, the column was washed with 16 ml of phosphate buffered saline (PBS; 10 mM $Na.PO_4$ pH 6.8/150 mM NaCl) and then 24 ml of 10 mM Tris, pH 8.0/1M NaCl. MGDF(1-174) was eluted with 40 ml of 20 mM CAPS (3-[Cyclohexylamino]-1-propanesulfonic acid) pH 10.5/1M NaCl/5 mM CHAPS (3-[(3-Cholamidopropyl) dimethylammonio]-1-propanesulfonate) in 6 ml fractions. The second fraction yielded a single band on a 14% SDS gel. This material was concentrated and buffer exchanged against a saline solution of 0.9% NaCl and was biologically active in vitro and in vivo. Other forms of CHO cell expressed MGDF were purified in a similar manner.

EXAMPLE 3

In vivo Biological Activity of rHuMGDF

Figure 4:
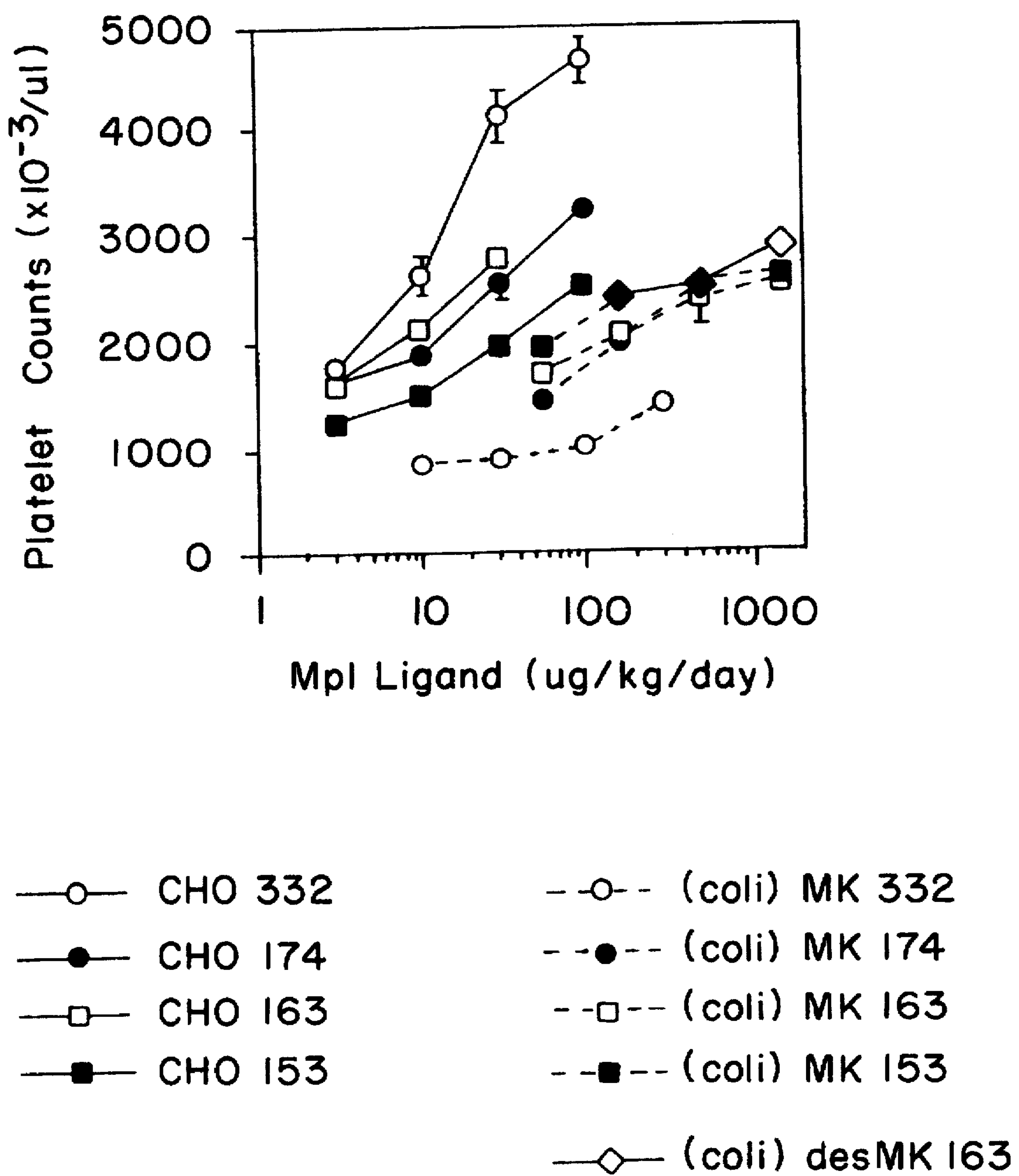
FIG. 4 shows in vivo activity of *E. coli* and CHO MGDF in normal mice, in terms of platelet counts. The data indicates that glycosylated MGDF (CHO material) has superior activity than non-glycosylated (*E. coli*) material. This may be a result of increased half-life for the glycosylated material. For example, CHO 332 stands for human MGDF amino acids 1-332 (FIG. 1) expressed in CHO cells.

Platelet counts from mice treated with various forms of r-HuMGDF were measured and the results are presented in FIG. 4. CHO-derived MGDF 1-332, 1-174, 1-163, and 1-153 were produced and purified by Mpl-receptor affinity chromatography. *E. coli*-derived Met-Lys-MGDF-1-332, Met-Lys-MGDF 1-174, Met-Lys-MGDF 1-163 and Met-Lys-MGDF 1-153 were produced and purified by conventional chromatography. The indicated concentration of each form was administered subcutaneously into normal, female Balb/c mice once daily for 5 days. Test bleeds from a small lateral cut in a tail vein were collected 24 hours after the last injection. Blood cell analyses were performed with a Sysmex electronic blood cell analyser (Baxter Diagnostics, Inc. Irvine, Calif.). Data are represented as the mean of determinations of 4 animals, ±standard error of the mean. Other blood cell parameters such as total white blood cell counts or red blood cell counts were not affected by these treatments (data not shown).

FIG. 4 shows platelet counts from mice treated with various forms of CHO cell-derived (solid lines) or *E. coli*-derived (dashed lines) recombinant human MGDF. Normal, female Balb/c mice were injected subcutaneously with the indicated concentration of rHuMGDF for 5 consecutive days. Twenty fours hours after the last injection, platelet counts were determined with an electronic cell counter. The results indicate that CHO cell expressed forms of MGDF have an increased in vivo activity relative to the same forms of MGDF produced in *E. coli*. As described in Example 6, the CHO cell expressed forms of MGDF all contain N and/or O-linked carbohydrate and the *E. coli* expressed MGDF forms do not. This indicates that the carbohydrate enhances the in vivo activity of MGDF. The increased in vivo activity conferred by the carbohydrate may be a result of increased circulatory half life, increased stability or a combination of both.

EXAMPLE 4

Construction of MGDF Analogs

Procedures for generating additional glycosylation sites for MGDF are described below.

The following oligonucleotide primers were synthesized for use in in vitro mutagenesis to prepare analogs N2–N14 (see Table 1 for the structures of these analogs):

N2—CCCATGTCAATCACAGCAGACT SEQ ID NO.: 5

N3—CTTCACAGCAACCTGAGCCAGT SEQ ID NO.: 6

N4—CAGTGCAACGAGACCCACCCTTTG SEQ ID NO.: 7

N5—GCCTACAAATGTCACGCTGCCTGCT SEQ ID NO.: 8

N6—CCCACTTGTAACTCATCCCTC SEQ ID NO.: 9

N7—CAACTGAACGCCACTTGTCTCTCA SEQ ID NO.: 10

N8—ACTTGTCTCAACTCCACCCTGGGGGA SEQ ID NO.: 11

N9—CTCCTGGGGAACCTTTCTGGA SEQ ID NO.: 12

N10—GACCACAAATCACACCGATCCCAAT SEQ ID NO.: 13

N11—ACCCTTTGTCTACAAATGTCACGCTGCCTGCT SEQ ID NO.: 14

N12—TCTCTCAAACCTCACGGGGGAGCTT SEQ ID NO.: 15

N13—TGGAAAAATCAGACGGAGGAGAC SEQ ID NO.: 16

N14—TGGAGGAGAACAAGACACAGGACAT SEQ ID NO.: 17

To construct m13mp18 MGDF 1-174, the gene of FIG. 2 was introduced into XbaI and SalI restriction enzyme digested m13mp18 DNA. Single stranded DNA was recovered from supernatants of *E. coli* strain RZ1032 infected by m13mp18 (MGDF 1-174) as described by Kunkel et al., *Methods in Enzymol.* 154:367 (1987) and Messing, *Methods in Enzymol.* 101:20 (1983). For in vitro mutagenesis approximately 0.5 μg of single-stranded DNA and 0.125 pmole of one of the synthetic primers described above were mixed with 6 μl of buffer (250 mM Tris pH 7.8, 50 mM $MgCl_2$, 50 mM dithiothreitol and 1% Bovine serum albumin (BSA-Pharmacia)). The primers were previously kinased with ATP and T4 polynucleotide kinase prior to addition. For annealing of the primer to the template, the reaction volume was adjusted to 10 μl with water, the mixture was heated to 65° C. for 5 minutes and then allowed to cool to room temperature. For the elongation reaction 2.5 μl of each of dTTP, dATP, dGTP and dCTP and 1 μl ATP (all at 10 μM) were added, followed by 1 μl (1 unit) of *E. coli* DNA polymerase (Klenow fragment) and 1 μl (1 unit) of T4 DNA ligase. The mixture was then incubated overnight at 14° C. and used to transform *E. coli* JM 109 (Yanisch-Perron et al. *Gene* 33, 103 (1985)) as described (Messing, supra).

To identify mutant clones by differential hybridization, plaques on nutrient agar were transferred to Gene Screen filters (New England Nuclear). The DNA was cross-linked to filters by irradiating them in a UV Stratalinker Model 1800 using the auto cross-link mode (Stratagene). They were then incubated for one hour in 6× SSC (0.9M NaCl/0.09M Na.citrate) containing 1% SDS at 60° C. For the hybridization, the oligonucleotide primer above (8 pmoles) was end-labeled with T4 polynucleotide kinase and γ $^{32}$P-labeled ATP and incubated with the filters overnight in 6× SSC, 0.5% SDS and 125 ug/ml herring sperm DNA. The hybridization temperatures were chosen according to estimates of oligonucleotide melting points. Generally the hybridization temperature was approximately 10° C. less than the melting point. The next day, the filters were washed two times with 6× SSC/1% SDS at hybridization temperature followed by two washes with 6× SSC at hybridization temperature and subjected to autoradiography. If necessary, the filters were then washed with 6× SSC at increasing temperatures until little or no hybridization was detected to plaques having the wild-type MGDF cDNA sequence. Clones that gave positive hybridization signals under these conditions were identified and retransfected into JM109 to isolate a pure clone. Dideoxy chain termination sequence analysis indicated that the mutations were present.

Double stranded m13 MGDF 1-174 DNAs carrying the desired changes were recovered from JM109 transfected cells with QIAGEN kits (Chatsworth, Calif.) using methods supplied by the manufacturer. The DNAs were digested with XbaI and SalI and the 605 bp MGDF DNA fragments were isolated. pDSRα2 was digested with XbaI and SalI. The vector fragment was isolated and ligated to the MGDF fragments above. Recombinant plasmids were identified by restriction analysis. The resulting plasmids (designated MGDF 1-174-X where X is the analog number) contain DNA encoding MGDF analogs having altered amino acid residues at the indicated positions. The resultant plasmids were then sequenced again to confirm the presence of the desired mutations.

An analog, MGDF 174-15 was constructed that had two additional N-linked glycosylation sites at positions 30 and 120. PDSRα2 MGDF 174-4 containing Asn30 and Thr32 mutations was digested with XbaI and PstI restriction enzymes and the approximately 385 nt DNA fragment was isolated. PDSRα2 MGDF 174-10 containing Asn120 and Thr122 mutations was digested with PstI and SalI restriction enzymes and the approximately 220 nt DNA fragment was isolated. pDSRα2 was digested with XbaI and SalI. The vector fragment was isolated and ligated to the MGDF fragments above. This resulted in PDSRα2 MGDF 174-15 that contains Asn30, Thr32, Asn120 and Thr122 substitutions.

These general procedures were used to construct the MGDF analogs shown in Table 1. The DNA sequence changes for each of the analogs are shown; otherwise the oligonucleotide primers used for mutagenesis had sequences complimentary to those of human MGDF.

TABLE 1

MGDF ANALOGS HAVING SITES FOR N-LINKED CARBOHYDRATE CHAINS

| Analog/Species No. | Amino Acid Substitution | Sequence Changes |
|---|---|---|
| N1 | NONE (amino acids 1-174 of FIG. 1) | NONE |
| N2 | $Leu^{22} \rightarrow Asn^{22}$ | CCT→AAT |
| N3 | $Arg^{25} \rightarrow Asn^{25}$ | AGA→AAC |
| N4 | $Pro^{30}$, $Val^{32} \rightarrow Asn^{30}$, $Thr^{32}$ | CCA, GTT→AAC, ACC |
| N5 | $Pro^{38}$, $Leu^{40} \rightarrow Asn^{38}$, $Thr^{40}$ | CCT, CTG→AAT, ACG |
| N6 | $Leu^{86} \rightarrow Asn^{86}$ | CTC→AAC |
| N7 | $Gly^{82}$, $Pro^{83} \rightarrow Asn^{82}$, $Ala^{83}$ | GGA, CCC→AAC, GCC |
| N8 | $Ser^{87}$, $Leu^{89} \rightarrow Asn^{87}$, $Thr^{89}$ | TCA, CTC→AAC, ACC |
| N9 | $Glu^{92} \rightarrow Asn^{92}$ | GAG→AAC |
| N10 | $Ala^{120}$, $Lys^{122} \rightarrow Asn^{120}$, $Thr^{122}$ | GCT, AAG→AAT, ACC |

TABLE 1-continued

MGDF ANALOGS HAVING SITES FOR N-LINKED CARBOHYDRATE CHAINS

| Analog/Species No. | Amino Acid Substitution | Sequence Changes |
|---|---|---|
| N11 | $Pro^{36}$, $Pro^{38}$, $Leu^{40}$→$Ser^{36}$, $Asn^{38}$, $Thr^{40}$ | CCT, CCT, CTG→TCT, AAT, ACG |
| N12 | $Ser^{88}Leu^{90}$→$Asn^{88}$, $Thr^{90}$ | TCC, CTG→AAC, ACG |
| N13 | $Thr^{53}$, $Met^{55}$→$Asn^{53}$, $Thr^{55}$ | ACC, ATG→AAT, ACG |
| N14 | $Thr^{58}$, $Ala^{60}$→$Asn^{58}$, $Thr^{60}$ | ACC, GCA→AAC, ACA |
| N15 | $Pro^{30}$, $Val^{32}$, $Ala^{120}$, $Lys^{122}$→$Asn^{30}$, $Thr^{32}$, $Asn^{120}$, $Thr^{122}$ | CCA, GTT, GCT, AAG→AAC, ACC, AAT, ACC |

Note:
Analogs N2–N15 are synonymously referred to herein as analogs 2–15. Further, as used herein, for example, [$Asn^{22}$] MGDF means that an asparagine has been substituted for the amino acid at position 22 in the particular MGDF species being considered, which is preferably a human sequence having at least amino acids 7–151 of FIG. 1 (including the preferred human MGDF sequences set forth herein above). Thus, substitution of an asparagine residue for a leucine residue at position 22 of MGDF 1-174 (human sequence) yields an MGDF analog that may be represented by [$Asn^{22}$] MGDF 1-174.

Plasmids designated pDSRα2 1-174-X (where X is the analog number) were constructed by inserting MGDF DNA into pDSRα2. The expression vector pDSRα2 is generally described in WO 90/14363(1990). pDSRα2 MGDF 1-174-X plasmids were made by digestion of pDSRα2 with XbaI and SalI. The vector fragment was isolated and ligated to the approximately 605 bp fragments containing the desired sequences.

EXAMPLE 5

Expression of MGDF and MGDF Analogs in COS Cells cDNA clones of human MGDF and MGDF analogs described in Table 1 were transferred into COS-1 cells (ATCC No. CRL-1650) by electroporation. COS-1 cells were harvested from semi-confluent dishes, washed with medium (Dulbecco's modified essential medium containing 10% fetal bovine serum and 1% L-glutamine/penicillin/streptomycin (Irvine Scientific)) and resuspended at $6\times10^6$ cells/ml. One half ml of cells was transferred to a 0.2 cm electroporation cuvette (Bio-Rad) and electroporated with a BTX Electroporation System Electrocell Manipulator 600 at 650 uF and 130 volts on the low voltage setting with 50 μg of plasmid DNA encoding the MGDF analog. The electroporated cells were plated on 100 mm tissue culture dish in 10 ml of medium. Twelve to twenty four hours after plating the medium was replaced with 10 ml of fresh medium. The conditioned medium was collected 3 to 5 days after electroporation.

EXAMPLE 6

Characterization of MGDF and MGDF Analogs

A. Determination of Carbohydrate Addition

A volume of supernatant containing approximately 30–60 ng MGDF or MGDF analog from COS cells transfected with MGDF analog cDNAs as described in Example 5 was immunoprecipitated overnight at room temperature with a rabbit anti-MGDF polyclonal antibody. In some cases where expression was low, a maximum volume of approximately 8–9 ml was used for immuno-precipitation. The antibody was raised to MGDF 1-163 that had been expressed and purified from *E. coli.* Thirty μl of 1:1 Protein A-Sepharose in phosphate buffered saline (PBS) containing 0.1% sodium azide was added to the immunoprecipitate and allowed to incubate for one hour at room temperature. The samples were centrifuged, washed with PBS and resuspended in SDS sample Buffer (0.125M Tris-HCl pH 6.8/4% SDS/20% glycerol/10% β-mercaptoethanol/0.001% bromophenol blue). The samples were analyzed by 12% SDS-polyacrylamide gel electrophoresis, transferred to nitrocellulose and subjected to Western analysis as described (Burnette et al., *Anal. Biochem.* 112:195–203 (1981); Elliott et al., *Gene* 79:167–180 (1989)) using a mouse anti-MGDF monoclonal antibody raised to a synthetic peptide corresponding to amino acid residues 1-31 of FIG. 1. The MGDF containing bands were visualized using an ECL kit (Amersham).

Figure 5:
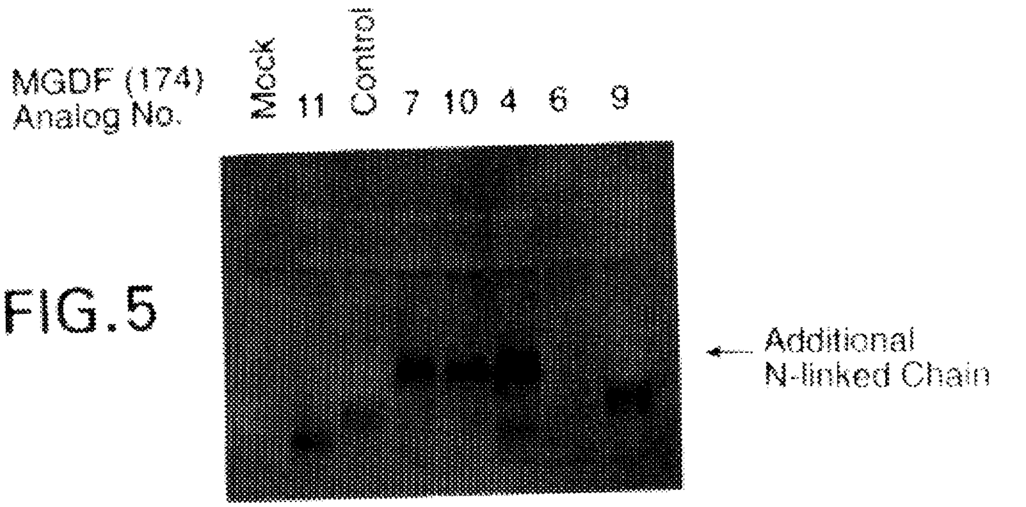
FIG. 5 shows a Western blot analysis of COS cell supernatants of recombinant human MGDF and analogs 4, 6, 7, 9, 10, and 11. The construction of the analogs is described in Example 4. Analogs 4, 7, 10 have at least one additional carbohydrate chain as evidenced by slower gel mobility. The analog numbers correspond to analog numbers provided in Table 1 (e.g., 11 corresponds to analog N11). The control is N1 in Table 1.
Figure 6:
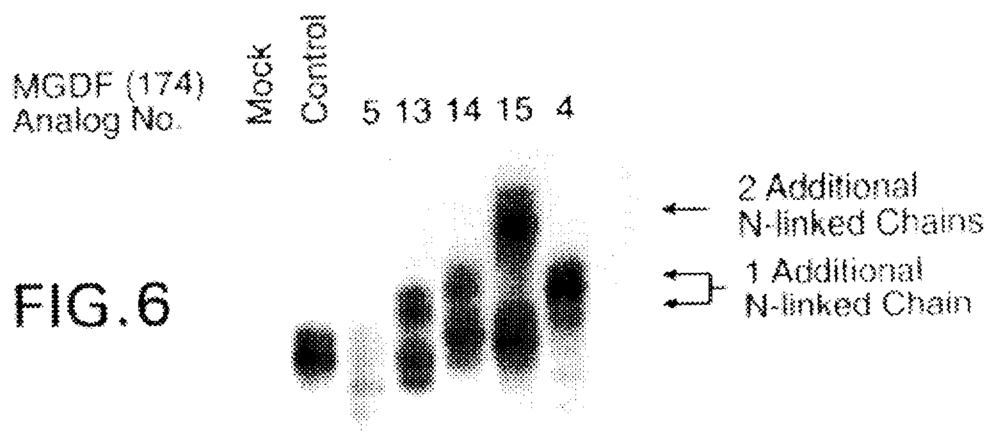
FIG. 6 shows a Western blot analysis of COS cell supernatants of recombinant human MGDF and analogs 4, 5, 13, 14, and 15. The construction of the analogs is described in Example 4. Analogs 4, 13, 14, and 15 have at least one additional carbohydrate chain as evidenced by slower gel mobility.

FIG. 5 shows that COS cell supernatants from cells transfected with analogs MGDF 174-4, MGDF 174-7 and MGDF 174-10 DNA revealed increased size compared to human sequence MGDF 174-1. FIG. 6 shows that COS cell supernatants from cells transfected with MGDF 174-13, MGDF 174-14 and MGDF 174-4 DNA also had increased size compared to human sequence MGDF. This increased size is indicative of an additional N-linked carbohydrate chain. MGDF analog 174-15 contains two additional N-linked glycosylation sites. FIG. 6 indicates that this analog has material with a size greater than analogs containing only 1 additional N-linked glycosylation. The sizes of the proteins were estimated from their mobility on SDS-PAGE relative to protein standards of known molecular weight. The estimated sizes of the larger bands calculated from FIG. 6 is shown in Table 2. This result indicates that MGDF 174-15 contains 2 additional N-lined chains. Western blot analyses of other selected analogs are also shown in FIG. 6.

TABLE 2

N-Linked Carbohydrate Estimates

| MGDF (1-174) Analog | Molecular Weight (Da) | Molecular Weight Shift (Da) (Over Native) | # of Potential N-Linked Chains (@4 KDa/Site) |
|---|---|---|---|
| N1 (Native) | 23500 | 0 | 0 |
| N4 | 28700 | 5200 | 1 |
| N7 | 27200 | 3700 | 1 |
| N10 | 27200 | 3700 | 1 |
| N13 | 26700 | 3200 | 1 |
| N14 | 28700 | 5200 | 1 |
| N15 | 33500 | 10000 | 2 |

Figure 7:
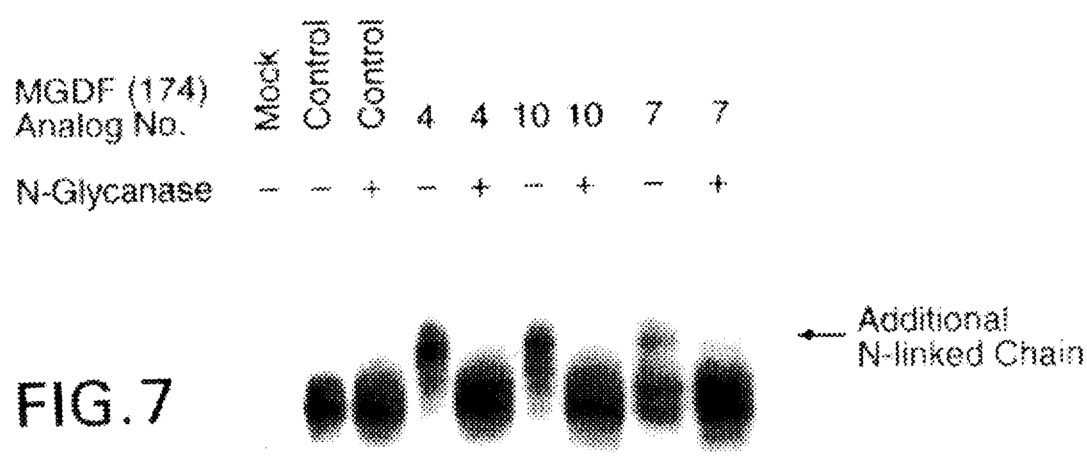
FIG. 7 shows a Western blot analysis of COS cell supernatants of human sequence MGDF and indicated MGDF analogs after treatment with N-glycanase. The results indicate that the analogs have differential glycosylation patterns.

An experiment was performed to show that the increased size of MGDF analogs is due to N-linked carbohydrate. COS cell conditioned medium containing MGDF was immunoprecipitated and washed with PBS as described above. To each tube was then added 10 μl 0.5% SDS and each sample was boiled for 3 minutes. Then the following components were added: 10.8 μl of 0.5M $NaPO_4$ pH 8.6, 5 μl of 7.5% nonidet P40 and 3 μl of 250 unit/ml N-glycanase (Genzyme). N-glycanase treatment removes N-linked carbohydrate. Samples were incubated for 6 hours at 37° C. The reaction was stopped by the addition of SDS-PAGE sample buffer and then subjected to SDS-PAGE Western analysis (12% acrylamide) using an anti-MGDF monoclonal antibody and an anti-mouse ECL Western Detection Kit (Amersham) as described above. An analysis of N-linked chains using this method is shown in FIG. 7 for human MGDF and MGDF analogs. Following treatment with N-glycanase the mobility on Western blot for MGDF 174-4, MGDF 174-7 and MGDF 174-10 was reduced to that of MGDF 174-1. As expected, treatment of MGDF 174-1 with N-glycanase had no effect on mobility because MGDF 174-1 has no N-linked glycosylation sites. These results indicate that the increased size observed is due to addition of N-linked carbohydrate.

B. Analysis of O-linked carbohydrate on MGDF

To analyze the contribution of O-linked carbohydrate to human MGDF, various forms of the protein were purified from CHO cell conditioned media as described above. Each form received ± treatment with O-glycanase (Glycopeptide alpha-N-acetylglactos-aminidase, Oxford GlycoSystems). O-glycanase removes O-linked carbohydrate from glycoproteins. The *E. coli* expressed version of each form was used as an unglycosylated control. To resolve the difference in molecular weight contributed by O-linked carbohydrate, it was necessary to remove any N-linked carbohydrate first. Since the full length version, MGDF 1-332, contains N-linked carbohydrate, the CHO cell expressed full length samples received N-glycanase (peptide-N4-(N-acetyl-beta-glucosaminyl) asparagine amidase) treatment as described above for COS cell expressed MGDF analogs, except that the N-glycanase treatment was an overnight incubation. Before proceeding with the O-glycanase treatment on full length (1-332) MGDF, the pH range of the sample was adjusted to pH 6.0–pH 7.0 with 1/15 volume of 100 mM acetic acid, pH 2.2. One microgram of protein was denatured by boiling for 3 minutes in SDS and incubated at 37° C. for 60 minutes with 1 U/ml neuraminidase (sialidase, from *Arthrobacter urefaciens*, Boehringer Mannheim) in 1 mM calcium acetate, pH 6.8 and 20 mM sodium phosphate, pH 6.8. Subsequent treatment with O-glycanase was done by adding 5 mU of enzyme in a final volume of 100 ul, followed by an overnight incubation at 37° C. Proteins (0.2 ug/lane) were separated by SDS-PAGE (15% acrylamide). Following transfer to 0.2 um nitrocellulose and overnight incubation with anti-MGDF polyclonal antibody the MGDF proteins were visualized using an anti-rabbit ECL Western Detection Kit (Amersham). FIG. 3 shows a Western blot of four different forms of human MGDF. Full length MGDF 1-332 is represented in lanes 1–3, MGDF 1-174 lanes 4–6, MGDF 1-163 lanes 7–9, and MGDF 1-153 lanes 10–12. Treatment with neuraminidase and O-glycanase, shown in lanes 2,5,8, and 11, reduced the molecular weight to that of unglycosylated materials, lanes 3,6,9, and 12. In every case the mobility increased to that of the unglycosylated version expressed in *E. coli*. These results indicate that the larger sized bands, in lanes 1,4,7, and 10 are due to O-linked carbohydrate. The molecular weights of each of the bands was estimated by comparing their mobilities to proteins of known molecular weight. As seen in Table 3 which shows estimated molecular weights of the different proteins, the apparent shift in mobility could account for as many as 14 O-linked carbohydrate chains (assuming 950 daltons/chain) for MGDF 1-332, 9 chains for MGDF 1-174, 4 chains for MGDF 1-163, and 2 chains for MGDF 1-153. The sample run in lane 2 is full length MGDF 1-332. It would appear that this protein was degraded, possibly due to extended incubation in glycoenzymes at 37° C. Therefore, the *E. coli* expressed unglycosylated version in lane 3 was used to calculate the approximate molecular weight of O-linked carbohydrate added to CHO cell expressed MGDF 1-332. These results are consistant with the presence of carbohydrate on all the CHO expressed forms of MGDF tested. The presence of O-linked carbohydrate was confirmed for CHO cell expressed MGDF 1-332, 1-174, and 1-163 by direct analysis of monosaccharide composition. Sialic acids, GalNAc and Gal were released from glycoproteins by acid hydrolysis. The monosaccharides were detected by high pressure anion exchange chromatography and pulsed amperometric detection. All three sugars were detected in each of the forms of MGDF. This result is indicative of the presence of sialic acid containing O-linked carbohydrate. This data correlates with the in vivo data as seen in FIG. 4 where CHO cell expressed forms of MGDF were all more active in vivo than the equivalent forms expressed in *E. coli*. Thus, the presence of carbohydrate enhances the in vivo activity of MGDF.

TABLE 3

O-Linked Carbohydrate Calculations

| MGDF Form | O-Glycanase Treatment (+/−) | Molecular Weight (Da) | Molecular Weight Shift | # of Potential O-Linked Chains (@950 Da/Chain) |
|---|---|---|---|---|
| 1-332 | − | 54200 | 13600 | 14 |
| " | *E. coli* version | 40600 | | |
| 1-174 | − | 24600 | 8600 | 9 |
| " | + | 16000 | | |
| 1-163 | − | 18400 | 3900 | 4 |
| " | + | 14500 | | |
| 1-153 | − | 15200 | 2300 | 2 |
| " | + | 12900 | | |

EXAMPLE 7

MGDF ELISA Assay

Polyclonal antibody production—New Zealand White rabbits were hyperimmunized over a period of three months with recombinant human MGDF 1-163 produced in *E. coli*. Antisera from six rabbits exhibiting high antibody titers were pooled and specific anti-MGDF antibodies were affinity purified.

Affinity purification—Recombinant human MGDF 1-163 was covalently attached to Actigel-ALD (Sterogene Bioseparations, Inc.) according to the manufacturer's instructions. An aliquot of the rabbit antisera pool was added to the MGDF affinity gel, and the slurry was agitated gently on a rocker platform overnight a 4°–8° C. Unbound serum proteins were washed from the gel bed with PBS and specifically bound anti-MGDF antibodies were then eluted with ImmunoPure Gentle Ag/Ab Elution Buffer (Pierce Chemical Co.) Recovered antibodies were dialyzed against several changes of PBS, then the antibody solution was concentrated in an Amicon stirred cell ultrafiltration unit and the resultant antibody concentrate was the source of specific anti-MGDF antibodies subsequently used for well coating and enzyme conjugate preparations.

ELISA reagents—Immulon 4 Removawell Strips (Dynatech Laboratories, Inc.) were coated with affinity purified rabbit anti-MGDF antibodies. Affinity purified antibodies were diluted in 0.1M sodium bicarbonate (freshly prepared pH about 8.2) to a concentration of 2.5 ug/ml. Each well received 100 ul of antibody and the plates were incubated for 24 hrs at room temperature in a sealed and humidified chamber. Then, 200 ul of a blocking solution consisting of 1% fetal bovine serum 5% sucrose in TEN (50 mM Tris 7.4/10 mM EDTA/150 mM NaCl) was added to each well and plates were incubated and additional 24 hrs at room temperature in a sealed and humidified chamber. Combined coating and blocking solutions were removed from the wells. An additional overcoating/blocking step was included: 300 ul of SuperBlock Blocking Buffer in PBS (Pierce Chemical Co.) was added to each well. After standing at room temperature for about 5 min. this solution was removed and the wells were allowed to air dry at room temperature for 24 hrs. The coated wells were stored in sealed plastic bags at 4°–8° C. until used in the MGDF ELISA.

Affinity purified anti-MGDF antibodies from a rabbit antisera pool were covalently coupled to horseradish peroxidase (HRPO) for use as the signal generating antibody. The affinity purified antibodies were derivatized with iminothiolane HCl (Fluka Chemical Corp.). Separately, HRPO was derivatized with N-succinimidyl 6-maleimidocaproate (Fluka Chemical Corp.). The two activated proteins were combined to permit covalent coupling. The reaction mixture was then chromatographed down a FPLC Superose 6 (Pharmacia) column to isolate the antibody:HRPO conjugate of the desired molecular weight (i.e. about 200 kD). Fractions containing the desired conjugate were combined and concentrated in a Centricon 30 (Amicon Division, W. R. Grace & Co.) and stored as a 50% glycerol solution at −20° C. This anti-MGDF Ab:HRPO concentrate was diluted into 2% fetal bovine serum in PBS for use in the ELISA. The final concentration of conjugate used in the ELISA was 250–500 ng/ml.

Recombinant human MGDF 1-163 produced in *E. coli* cells, was used for the preparation of standards. This MGDF was diluted into 2% fetal bovine serum (Sigma Chemical Co.) in TEN buffer containing 0.05% thimerosal as a preservative. Standards prepared contained 1.0, 0.5, 0.25, 0.125 and 0.062 ng/ml MGDF.

Assay-100 ul of MGDF standards or samples was added to wells then incubated for 18–24 hrs at room temperature in a sealed and humidified chamber. The well contents and residual solution were then removed and the wells washed once with wash solution (0.05% Tween 20 in TEN buffer). Anti-MGDF Ab:HRPO conjugate solution (100 ul) was added to each well and then incubated for 2 hrs at room temperature in a sealed and humidified chamber. The contents of wells were removed then washed 4 times with 0.05% Tween 20 in TEN buffer. For color development, 100 ul of TMB/peroxide substrate solution (Kirkegaard & Perry Solutions A & B mixed 1:1) was added and incubated for 20 min at room temperature. The reaction was stopped by addition of 100 ul stop solution (0.5N sulfuric acid) and the absorbance was read at 450 nm on microtiter plate reader. Concentrations of MGDF in samples were calculated from a standard curve generated by using a curve fit program.

EXAMPLE 8

Biological Activity of MGDF 1-174 Analogs in a Short-Term Liquid Culture Megakaryocyte Assay Analogs of MGDF(1-174) were prepared as described above and assayed for their ability to stimulate the growth of megakaryocytes in liquid culture. CD34 selected cells isolated from human leukapheresis units (Nichol et al., *Stem Cells* 12:494–505 (1994)) were plated at $2\times10^5$/ml in culture medium (IMDM/1% Pen-Strep Glutamine/1% Non-essential Amino Acids/1% MEM Na-Pyruvate/1% MEM Vitamins/10% deionized BSA/10% normal human AB plasma/10 uM alpha-thiacylglycerol/20 ug/ml L-Asparagine). In addition, 1.5 ul of COS-1 conditioned medium containing MGDF(1-174) or MGDF(1-174) analog was added to each well. The final volume was 15 ul in Terasaki-style microtiter tissue culture plates (Vangard International). Cells were incubated at 37° C. for eight days in humidified boxes in 5% $CO_2$, fixed directly to the culture wells with 1% glutaraldehyde, and then incubated with a monoclonal antibody cocktail consisting of anti-GPIb, anti-GPIIb, (Biodesign) and anti-GPIb (Dako, Carpinteria, Calif.) The immune reaction was developed with a streptavidin-β-glactosidase detection system (HistoMark, Kirkegaard and Perry). Megakaryocytes, identified by the darker color (blue in actual photographs), appear in FIG. 8.

Panels A and D of FIG. 8 are the positive and negative controls respectively. The well pictured in panel A received 37.5 pg of wild type MGDF 1-174 COS-1 conditioned medium and shows substantial megakaryocyte growth. Panel D received 1.5 ul of COS-1 mock conditioned medium and shows no growth. Panels B and C of FIG. 8 are MGDF 1-174 analogs 7 and 10 respectively. Panel B received 9.0 pg of MGDF COS-1 conditioned medium while panel C received 27 pg and both show excellent megakaryocyte growth.

This experiment indicates that the analogs of MGDF tested are capable of stimulating the growth of human megakaryocytes in vitro.

EXAMPLE 9

Biological Activity of MGDF 1-174 Analogs in an In Vitro Cell Proliferation Assay Analogs of MGDF(1-174) were prepared as described above and assayed for their ability to stimulate the proliferation of 32D-MPL cells. To construct 32D-MPL cells, the full length human Mpl receptor sequence (Vigon, I., et al., *PNAS* 89:5640–5644 (1992)) was subcloned into an expression vector containing the transcriptional promoter of Moloney Murine Sarcoma virus. Six ug of this construct and 6 ug of an amphotrophic retroviral packaging construct (Landau, N. R., Littman, D. R., *Journal of Virology* 66:5110–5113 (1992)) were transfected into $3\times10^6$ 293 cells using a $CAPO_4$ mammalian transfection kit (Stratagene). The same cells were retransfected after 2 days and again after 4 days. The day after the last transfection the 293 cells were cocultivated with the IL-3 dependent murine cell line (32D, clone 23; Greenberger et al., *PNAS* 80:2931–2936 (1983)). After 24 hours, the 32D cells were rescued and banded in a BSA gradient (Path-o-cyte; Miles Inc.). Cells were expanded in 1 ng/ml murine IL-3 and then were selected for growth in 20% APK9 serum (Bartley et al., *Cell* 77:1117–1124 (1994). Cells were sorted for cell surface expression of receptor by FACS using a polyclonal rabbit antipeptide (MPL) serum. These cytokine dependent murine 32D-MPL cells are responsive to MGDF. 32D-MPL cells were grown in MEM medium containing 10% Fetal Clone II Serum (Hyclone Laboratories) and 1.0 ng/ml muIL3 to a cell density of $1\times10^6$ cells/ml. Cells were collected by centrifugation (approx. 500×G) and washed twice in growth medium lacking muIL3 and resuspended at $1\times10^5$ cells/ml. An extended twelve point MGDF standard curve was prepared using rHuMGDF (1-163) and ranges from 5000 to 1 pg/ml. A volume of 100 ul of each dilution of standard MGDF or assay sample was added to appropriate wells of a 96 well microtiter tissue culture plate containing 100 ul of resuspended cells (10,000 cells/well) and incubated in a humidified incubator at 37° C. and 10% $CO_2$. After 48 hours, 40 ul of MTS reagent (Aqueous Non-Radioactive Cell Proliferation Kit, Promega) was added to each well and 14–18 hours later the plates were read on a plate reader at 490 nM. The in vitro activity in samples was calculated from a dose response curve for each sample. One unit was defined as the amount of MGDF in each sample required to give 50% of maximal stimulation. Specific activity was calculated by dividing the biological activity in units/ml by the MGDF concentration in ng/ml as determined by MGDF ELISA.

The specific biological activity of MGDF analogs transfected and expressed in COS cells is shown in Table 4. The effect of the amino acid substitutions on carbohydrate addition is also summarized. Purified human sequence MGDF has an in vitro activity that was 200–300 unit/ng as determined by the above-mentioned assays. It is apparent from Table 4 that MGDF analogs containing additional N-linked carbohydrate are expressed as well as native sequence MGDF even when they contain additional carbohydrate chains (as determined in Example 6, Section A) e.g. MGDF 174-4 and MGDF 174-10. Both of these analogs retained full in vitro biological activity also. Therefore the MGDF analogs containing N-linked carbohydrate can be expressed normally in mammalian cells and they can have normal or enhanced in vitro biological activity.

TABLE 4

| MGDF Form | Sequence | Number of N-linked chains(a) | Elisa (ng/ml)(b) | In Vitro Activity (units/ml)(c) | Specific Activity (units/ng)(d) |
|---|---|---|---|---|---|
| MOCK | NONE | 0 | <0.08 | <10 | <125 |
| 174-1 | Native | NA | 25 | 5375 | 215 |
| 174-1 | Native | 0 | 31.4 | 8800 | 280 |
| 174-1 | Native | 0 | 31.75 | NA | NA |
| 174-2 | N22 | 0 | NA | NA | NA |
| 174-3 | N25 | NA | 1.85 | 636 | 344 |
| 174-4 | N30T32 | 1 | 38 | 8830 | 232 |
| 174-4 | N30T32 | 1 | 24 | NA | NA |
| 174-5 | N38T40 | 0 | 1.2 | <10 | <8 |
| 174-6 | N86 | 0 | 0.44 | <10 | <22 |
| 174-7 | N82A83 | 0 to 1 | 6 | 2660 | 443 |
| 174-7 | N82A83 | 0 to 1 | 4.7 | 3080 | 655 |
| 174-9 | N92 | 0 | 10.5 | 1970 | 188 |
| 174-10 | N120T122 | 1 | 20.4 | 5943 | 291 |
| 174-10 | N120T122 | 1 | 33.7 | 9690 | 288 |
| 174-11 | S36N38T40 | NA | <0.625 | <10 | <16 |
| 174-11 | S36N38T40 | 0 | 1.3 | <10 | <8 |
| 174-13 | N53T55 | 0 to 1 | 67 | 18000 | 269 |
| 174-14 | N58T60 | 0 to 1 | 17.9 | 4850 | 271 |
| 174-15 | N30T32N120T122 | 0 to 2 | 26 | 6420 | 247 |

NOTES

[a]The number of additional N-linked chains was estimated based upon the mobility of the analog polypeptides in SDS gels as described in Example 6.
[b]Quantities of MGDF analogs in CHO cell supernatants were determined by ELISA assay as described in the Examples.
[c]In vitro activity was determined by measuring stimulation of thymidine uptake in 32D cells dependent on MGDF for growth.
[d]Ratio of in vitro activity of MGDF analog as measured by proliferation assays to amount of MGDF analog measured by MGDF ELISA.
N.A. Not available.

While the invention has been described in what is considered to be its preferred embodiments, it is not to be limited to the disclosed embodiments, but on the contrary, is intended to cover various modifications and equivalents included within the spirit and scope of the appended claims, which scope is to be accorded the broadest interpretation so as to encompass all such modifications and equivalents.

What is claimed is:

1. An isolated DNA having a nucleotide sequence encoding an analog of megakaryocyte growth and development factor (MGDF), wherein (a) said MGDF analog comprises a sequence of amino acids selected from the group consisting of amino acid sequences 7-151 through 1-332, inclusive of SEQ ID NO: 1, (b) said analog of MGDF has at least one added N-linked glycosylation site in said sequence of amino acids, (c) said MGDF analog has a biological activity of specifically stimulating or increasing megakaryocytes or platelets, and (d) said at least one added N-linked glycosylation site is selected from the group consisting of:

[Asn30, Thr32];
[Asn82, Ala83];
[Asn120, Thr122];
[Asn53, Thr55];
[Asn58, Thr60]; and
[Asn30, Thr32, Asn120, Thr122].

2. An isolated DNA of claim 1, wherein the MGDF analog has an amino acid sequence selected from the group consisting of:

MGDF1-332 amino acids 1-332 of SEQ ID NO: 1;
MGDF1-191 amino acids 1-191 of SEQ ID NO: 1;
MGDF1-183 amino acids 1-183 of SEQ ID NO: 1;
MGDF1-174 amino acids 1-174 of SEQ ID NO: 1;
MGDF1-163 amino acids 1-163 of SEQ ID NO: 1;
MGDF1-153 amino acids 1-153 of SEQ ID NO: 1;
MGDF1-152 amino acids 1-152 of SEQ ID NO: 1;
MGDF1-151 amino acids 1-151 of SEQ ID NO: 1;
MGDF7-332 amino acids 7-332 of SEQ ID NO: 1;
MGDF7-191 amino acids 7-191 of SEQ ID NO: 1;
MGDF7-183 amino acids 7-183 of SEQ ID NO: 1;
MGDF7-174 amino acids 7-174 of SEQ ID NO: 1;
MGDF7-163 amino acids 7-163 of SEQ ID NO: 1;
MGDF7-153 amino acids 7-153 of SEQ ID NO: 1;
MGDF7-152 amino acids 7-152 of SEQ ID NO: 1; and
MGDF7-151 amino acids 7-151 of SEQ ID NO: 1.

3. An isolated DNA of claim 2, wherein the MGDF analog has an amino acid sequence consisting of amino acids 1-163 of SEQ ID NO: 1.

4. An isolated DNA of claim 2, wherein the MGDF analog has an amino acid sequence consisting of amino acids 1-174 of SEQ ID NO: 1.

5. An isolated DNA according to claim 2, which encodes MGDF 1-174.

6. A plasmid containing a DNA according to any of claims 1–5.

7. A eukaryotic cell containing a plasmid according to claim 6.

* * * * *

UNITED STATES PATENT AND TRADEMARK OFFICE

CERTIFICATE OF CORRECTION

PATENT NO. : 5,696,250

DATED : December 9, 1997

INVENTOR(S) : Steven G. Elliott

It is certified that error appears in the above-indentified patent and that said Letters Patent is hereby corrected as shown below:

In Figure 1A, line 1, change "53" to --59--; line 3, change "70" to --60--.

In Figure 1C, line 10, change "329" to --328--; line 10, at end of column, add --332--.

In Column 10, line 32, change "MGDF-1-332" to --MGDF 1-332--.

In Column 34, line 55, after "encodes" insert --[Asn30, Thr32, Asn120, Thr122]--.

Signed and Sealed this

Twenty-third Day of June, 1998

Attest:

BRUCE LEHMAN

*Attesting Officer* — *Commissioner of Patents and Trademarks*